(12) United States Patent
Sørensen et al.

(10) Patent No.: US 11,826,019 B2
(45) Date of Patent: Nov. 28, 2023

(54) TIP PART FOR A MEDICAL INSERTION VISION DEVICE

(71) Applicant: AMBU A/S, Ballerup (DK)

(72) Inventors: Morten Sørensen, Ballerup (DK); Hans Jochumsen, Allerød (DK)

(73) Assignee: AMBU A/S, Ballerup (DK)

( * ) Notice: Subject to any disclaimer, the term of this patent is extended or adjusted under 35 U.S.C. 154(b) by 0 days.

(21) Appl. No.: 17/675,963

(22) Filed: Feb. 18, 2022

(65) Prior Publication Data
US 2022/0287546 A1    Sep. 15, 2022

(30) Foreign Application Priority Data
Mar. 12, 2021  (EP) ..................................... 21162208

(51) Int. Cl.
*A61B 1/00* (2006.01)
*A61B 1/05* (2006.01)
*A61B 1/06* (2006.01)

(52) U.S. Cl.
CPC .............. *A61B 1/0008* (2013.01); *A61B 1/05* (2013.01); *A61B 1/0676* (2013.01); *A61B 1/0684* (2013.01)

(58) Field of Classification Search
CPC . A61B 1/0008; A61B 1/00096; A61B 1/0011; A61B 1/05; A61B 1/051; A61B 1/0684; A61B 1/07
See application file for complete search history.

(56) References Cited

U.S. PATENT DOCUMENTS

| 5,609,561 A | 3/1997 | Uehara et al. |
| 6,547,721 B1 * | 4/2003 | Higuma ............. G02B 23/2492 600/110 |

(Continued)

FOREIGN PATENT DOCUMENTS

| JP | H0998944 A | 4/1997 |
| JP | 2949044 B2 | 9/1999 |

(Continued)

OTHER PUBLICATIONS

Extended search report in European Application No. 21162208.9 dated Aug. 25, 2021, 9 pages.

*Primary Examiner* — Aaron B Fairchild
*Assistant Examiner* — Julianna J Nicolaus
(74) *Attorney, Agent, or Firm* — Faegre Drinker Biddle & Reath LLP

(57) ABSTRACT

A tip part for a medical insertion vision device, a method of making the tip part, and a visualization system including the medical insertion vision device. The tip part includes an exterior housing having a distal front wall and a circumferential wall, the distal front wall and the circumferential wall enclosing an interior spacing having a camera compartment at a distal end and a potting compartment proximal of the camera compartment; a camera assembly positioned in the camera compartment, the camera assembly comprising an image sensor and a lens stack positioned distally of the image sensor, the image sensor having a proximal end; a sealing material that forms a seal that seals the camera compartment from the potting compartment; and a potting material in the potting compartment, the sealing material preventing the potting material from extending father distally than the proximal end of the image sensor.

23 Claims, 11 Drawing Sheets

(56) References Cited

U.S. PATENT DOCUMENTS

| | | |
|---|---|---|
| 8,896,681 B2 | 11/2014 | Ishida |
| 9,220,400 B2 | 12/2015 | Petersen |
| 10,149,602 B2 | 12/2018 | Daher et al. |
| 2004/0027459 A1 | 2/2004 | Segawa et al. |
| 2007/0249907 A1* | 10/2007 | Boulais .................. A61B 5/064 |
| | | 600/179 |
| 2008/0266441 A1* | 10/2008 | Ichimura ................ H04N 23/55 |
| | | 348/340 |
| 2010/0261961 A1 | 10/2010 | Scott et al. |
| 2012/0082842 A1* | 4/2012 | Hirano .................. A61L 15/585 |
| | | 428/325 |
| 2013/0102846 A1 | 4/2013 | Sjostrom et al. |
| 2014/0073853 A1 | 3/2014 | Swisher et al. |
| 2016/0030693 A1 | 2/2016 | Nakatate et al. |
| 2017/0325663 A1* | 11/2017 | Levy .................... A61B 1/0615 |
| 2018/0242822 A1* | 8/2018 | Hamazaki .......... A61B 1/00096 |
| 2019/0282070 A1* | 9/2019 | Vilhelmsen ........ A61B 1/00096 |
| 2020/0100663 A1 | 4/2020 | Jensen et al. |
| 2020/0178777 A1 | 6/2020 | Konwitz et al. |
| 2020/0405137 A1 | 12/2020 | Sørensen et al. |
| 2021/0105386 A1 | 4/2021 | Satake |
| 2021/0127958 A1* | 5/2021 | Wakabayashi ....... A61B 1/0011 |

FOREIGN PATENT DOCUMENTS

| | | | |
|---|---|---|---|
| JP | 2009125528 A * | 6/2009 | |
| JP | 4530744 B2 | 8/2010 | |
| JP | 6205324 B2 | 9/2017 | |
| WO | WO-2021176551 A1 * | 9/2021 | ........... G02B 23/243 |

* cited by examiner

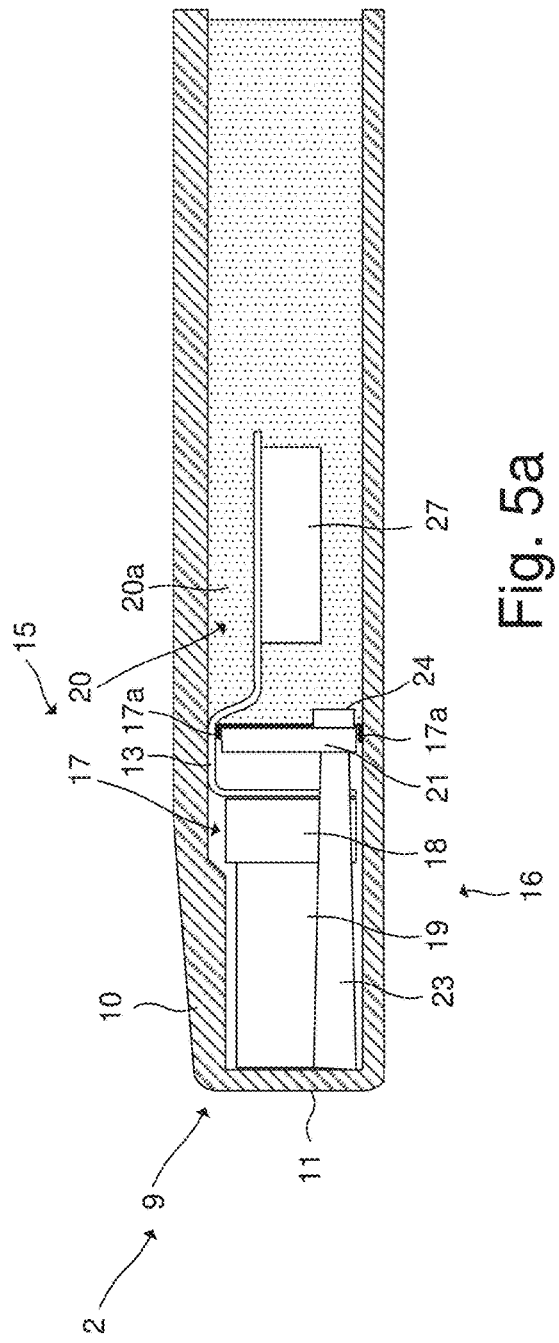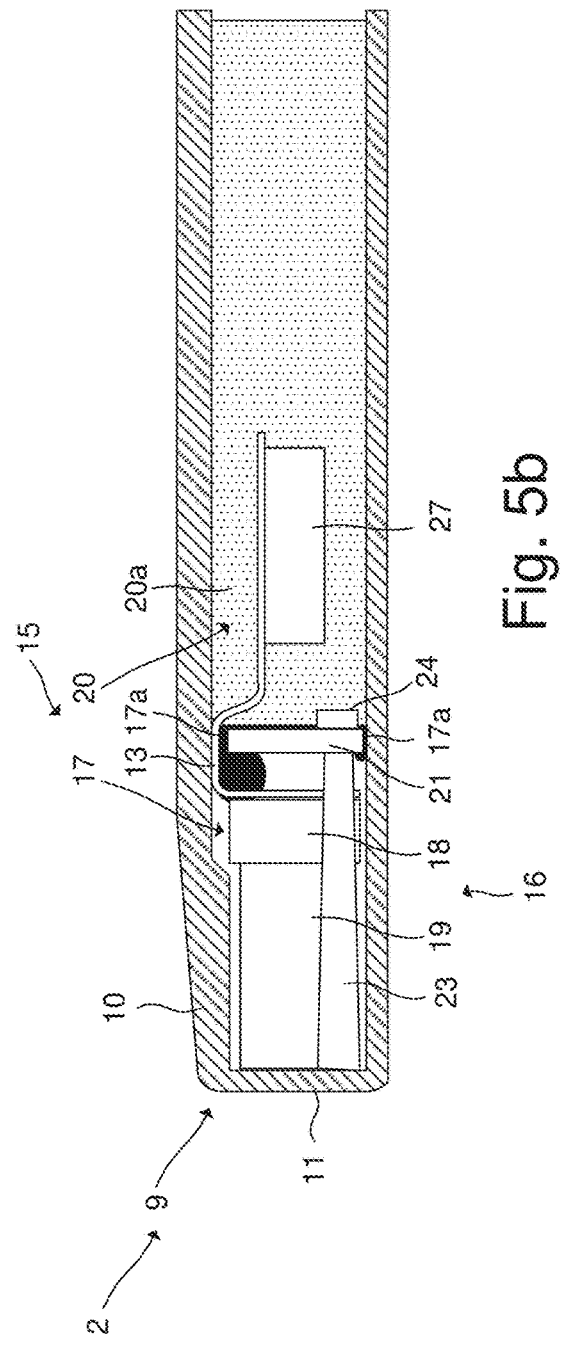

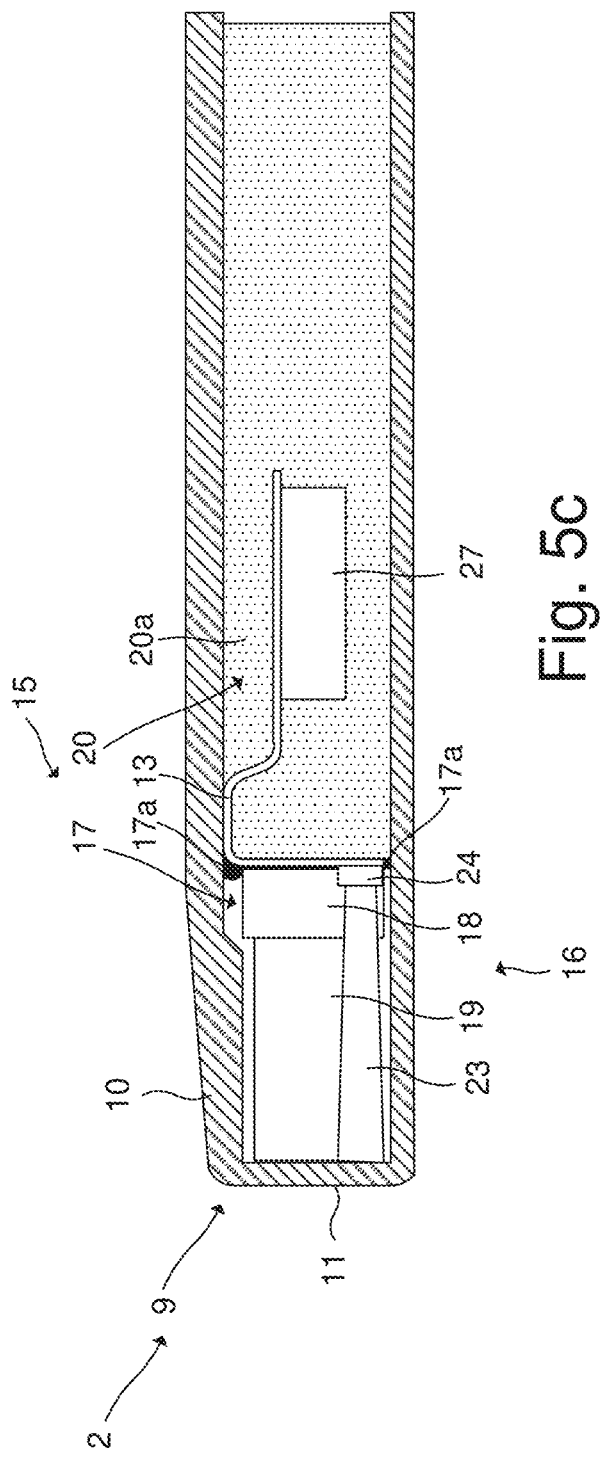

TIP PART FOR A MEDICAL INSERTION VISION DEVICE

CROSS-REFERENCE TO RELATED APPLICATIONS

This application claims priority from and the benefit of European Application No. 21162208.9, filed Mar. 12, 2021, which is incorporated herein by reference in its entirety.

TECHNICAL FIELD

The present disclosure relates to insertable medical vision devices, such as, but not limited to, endoscopes, catheters with a built-in camera, such as endotracheal tubes, feeding probes with a built-in camera, and medical tools comprising a camera, more specifically to a method of manufacture of a tip part of such a vision device, a tip part of such a vision device, and to a medical insertion vision device with such a tip part.

BACKGROUND

Medical insertion vision devices, such as endoscopes and catheters, are well known for visually inspecting difficult to access places such as human body cavities.

Typically, an endoscope comprises an elongated insertion tube with a handle at the proximal end, as seen from the operator, and visual inspection means, such as a built-in camera including an image sensor, at a distal end of the elongated insertion tube. This definition of the terms distal and proximal, i.e. "proximal" being the end closest to the operator and "distal" being the end remote from the operator, as used herein for medical insertion vision devices in general, is adhered to in the present specification. Electrical wiring for the camera and other electronics, such as one or more LEDs accommodated in the tip part at the distal end, runs along the inside of the elongated insertion tube from the handle of the device to the tip part. A working or suction channel may run along the inside of the insertion tube from the handle to the tip part, e.g. allowing liquid to be removed from the body cavity or allowing for insertion of surgical instruments or the like into the body cavity. The suction channel may be connected to a suction connector, typically positioned at a handle at the proximal end of the insertion tube.

To be able to manoeuvre the endoscope inside the body cavity, the distal end of the device may comprise a bending section with increased flexibility, e.g. a number of articulated segments of which the tip part or an external housing thereof may form the distalmost segment. The manoeuvring of the device inside the body is typically done by tensioning or slacking one or more pull wires also running along the inside of the elongated insertion tube from the tip part through the remainder of articulated segments to a control arrangement of the handle.

On the other hand, a catheter with a built-in camera typically comprises a single or dual lumen tube for insertion into anatomic body cavities. The camera together with a light source and a cleaning nozzle arrangement for illumination and facilitation of vision may be arranged in a tip part of a separate dedicated peripheral lumen of the catheter e.g. in a dedicated camera lumen. The dedicated camera lumen may be provided near a distal end of a working channel lumen comprising a working channel, so that the camera may provide vision of the working channel lumen and/or its surroundings during insertion of the catheter to ensure correct insertion. The camera may also be used for providing vision and monitoring of a specific target area within the anatomic body cavity when inserted. Once the catheter has been inserted to the correct position, one or more inflatable cuffs may be inflated to seal against air leakage and aspiration of gastric contents, blood, secretions, and other fluids, as well as to facilitate retention of the position. As described herein, the working channel may allow passage of fluids, e.g. air for ventilation of a patient and/or insertion of medical tools. The manoeuvring of the catheter inside the body is typically done by moving and adjusting the catheter by hand or may be facilitated by tools. Catheters may for example be made of plastic, rubber, polymers, or silicone together.

As the name indicates, insertable medical vision devices are used for providing vision inside anatomic cavities, such as lungs or other human body cavities of a patient. Modern insertable medical vision devices are therefore typically equipped with a light source and a camera or vision receptor including a vision or image sensor. Provided that sufficient light is present, it is possible for the operator to see where the device is inserted or steered and to set the target of interest once the tip has been advanced thereto. This therefore normally requires illumination of the area in front of the tip of the device, in particular the field of vision of the camera(s). The light source, such as a light emitting diode (LED) or an optical fibre, may provide illumination.

Additionally, when, as in the present disclosure, parts of the device accommodating electronic components are intended to be inserted into a human body cavity, these parts should furthermore be sealed appropriately in a watertight manner. This is particularly the case for a tip part accommodating a camera, LED(s), and/or other delicate electronics, prone to malfunction or destruction if exposed to humidity.

SUMMARY

A first aspect of this disclosure relates to a method of manufacture of a tip part, the tip part being for forming at least part of a tip of a medical insertion vision device, such as an insertion endoscope or a catheter, the method comprising: providing an exterior housing of the tip part having an open proximal end for connection to other parts of the medical insertion vision device, such as an insertion tube, the housing further having a distal front wall and a circumferential wall, the circumferential wall extending from the distal front wall to the proximal end of the housing, the distal front wall and the circumferential wall enclosing an interior spacing of the tip part; inserting a camera assembly of the tip part into a distal camera compartment of the interior spacing, the camera assembly comprising an image sensor and a lens stack, the lens stack being positioned distally of the image sensor, whereby the image sensor can provide an image from an object to be investigated; sealing the camera compartment towards a proximal potting compartment of the interior spacing by means of a sealing material; and potting a potting material into the potting compartment, the sealing of the camera compartment preventing the potting material from reaching the camera compartment, the camera compartment containing the lens stack and the image sensor, wherein, after the potting of the potting material, the potting material does not extend farther distally than to a proximal end of the image sensor.

In this way a tight sealing of the camera compartment may be achieved which can prevent potting material from entering the camera compartment and potentially interfering or obstructing light from passing through the lens stack and reaching the image sensor.

The tip parts according to this disclosure may make it possible to reduce external dimensions of the tip parts and may reduce costs and time in manufacture.

The tip of the medical insertion vision device may be a distal tip of the medical insertion vision device.

The tip part may further be attached to a bending section having a distal end segment, the distal end of the bending section and the proximal open end of the housing potentially being adjoined to each other.

The tip part, may be a tip part for forming at least part of a tip of a disposable medical insertion vision device. The term "disposable" may be understood as single-use i.e. a device that is to be discarded after using it once.

An exterior sleeve or an outer sheath of the insertion tube of the medical insertion vision device may be attached to the exterior or the interior of the circumferential wall of the housing.

The exterior housing may be an outer most wall of the tip part. The exterior housing may be cup-shaped, the cup-shape being formed by the distal front wall and the circumferential housing wall. The exterior housing may fluid seal the interior spacing.

The distal front wall may be a distal most wall of the tip part. The distal front wall may define a distal most part of the tip part. The distal front wall may be positioned oppositely from the proximal end of the housing. The distal front wall may be at least partly coinciding with a distal end of the tip part.

The circumferential wall may have a polygonal e.g. square, pentagonal, hexagonal, heptagonal, octagonal, nonagonal, decagonal etc., oval, cylindrical or circular-cylindrical outer and/or inner surface. The circumferential housing wall may comprise or be a circumferentially extending polygonal e.g. square, pentagonal, hexagonal, heptagonal, octagonal, nonagonal, decagonal etc., oval, cylindrical, or circular-cylindrical wall.

The circumferential housing wall may extend in a distal-proximal direction. The distal front wall may extend in a transverse direction, the transverse direction being transverse to the distal-proximal direction.

The interior spacing may be a volume enclosed by the distal front wall and the circumferential wall. The term "enclosing an interior spacing" may be understood as surrounding the interior spacing. The spacing may be completely enclosed i.e. encapsulated with only an opening at the open proximal end and/or any openings at potential outlets and/or inlets of the tip part.

The camera assembly may be inserted into the camera compartment to a final position of the camera assembly in the manufactured tip part. The camera assembly may be positioned to abut a camera window and/or a proximal surface of the front wall and/or an interior surface of the circumferential wall. The camera assembly may be inserted from the open proximal end of the housing. The camera assembly may be inserted into the camera compartment from the open proximal end of the exterior housing and potentially through an open proximal end of the camera compartment, such that the image sensor and lens stack are positioned within the camera compartment.

The camera compartment may be a distal volume of the interior spacing. The distal volume may be positioned in a distal-most two thirds, potentially a distal-most half, or distal-most third of the exterior housing and/or interior spacing.

The camera compartment may have an open proximal end. The camera assembly and/or closing element may be inserted into the camera compartment from the open proximal end of the camera compartment. The proximal end of the camera compartment may be positioned distally of the proximal open end of the exterior housing. The proximal end of the camera compartment may be positioned a distance equal to or more than $1/20$, $1/19$, $1/18$, $1/17$, $1/16$, $1/15$, $1/14$, $1/13$, $1/12$, $1/11$, $1/10$, $1/9$, $1/8$, $1/7$, $1/6$, $1/5$, $1/4$, $1/3$, $2/5$, $1/2$, $3/5$, $2/3$, $4/5$, or $9/10$ of a total housing length of the housing. The total housing length may extend in a proximal-distal direction.

The term "wherein, after the potting of the potting material, the potting material does not extend farther distally than to a proximal end of the image sensor" may alternatively be worded, or may further involve, "wherein, after the potting of the potting material, the potting material does not extend farther distally than to a proximal level of a proximal end of the image sensor" or "whereby, after the potting of the potting material, the potting material does not extend distally beyond a proximal end of the image sensor" or "wherein the potting compartment does not extend farther distally than to a proximal end of the image sensor".

The step of potting a potting material may substantially fill the potting compartment with the potting material. The potting compartment may be filled to an upper potting level. The upper potting level may substantially coincide with a proximal opening of the potting compartment. The proximal opening of the potting compartment may substantially coincide with the proximal opening of the exterior housing.

The potting compartment may be defined by a proximal volume of the interior spacing, the proximal volume being positioned proximally of the sealing material, potentially proximally of the closing element. The potting compartment may be positioned between the proximal opening of the exterior housing and proximally of the sealing material and/or closing element.

When the tip part comprises a working channel opening and/or working channel, a working channel tube may be inserted into the tip part, potentially into the working channel opening and/or working channel of the tip part before the step of potting the potting material, potentially before the step of applying the sealing material. The working channel or working channel tube may be inserted into the tip part after applying the sealing material.

The interior spacing may be defined by a volume enclosed by the exterior housing.

The term "potting" may involve substantially completely filling the potting compartment with a potting material.

The lens stack may include two or more lenses. The lenses may be stacked in a proximal-distal direction. The lenses may optically change light, such as to focus light onto an image sensor.

The term "exterior" in the term "exterior housing" may be understood as the housing being exterior in relation to the components or elements positioned inside the housing as defined above. The circumferential wall may be cylindrical and/or tubular. For an exterior housing including such a circumferential wall, the term "open end" may involve that the housing includes substantially no transversely extending part at a proximal end of the circumferential wall which would potentially cover an end opening of the tube. Alternatively, such a transversely extending part or wall may be included in the exterior housing, the open end being provided as an opening in such part or wall.

The medical insertion vision device may be an insertion endoscope.

The medical insertion vision device may be a catheter such as an endotracheal tube. The endotracheal tube may be a single-lumen endotracheal tube or a dual-lumen endotracheal tube. A catheter comprising a camera may be an insertion endoscope. An endotracheal tube comprising a camera may be an insertion endoscope.

The method may comprise the step of applying the sealing material. The method may comprise the step of curing the sealing material. The sealing material may be cured immediately after being applied, potentially such that it is cured before flowing into a sealing gap. The sealing material may be cured by heat and/or by activation through an activation agent and/or by light exposure e.g. UV, laser, and/or the like.

The step of potting may occur subsequent to curing the sealing material. The potting material may be cured subsequent to being potted. This potting material may be the only potting material in the tip part.

A proximal-distal direction may extend from a proximal end of the tip part to a distal end of the tip part. A distal-proximal direction may extend from a distal end of the tip part to a proximal end of the tip part.

The circumferential wall may extend in the distal-proximal direction. The distal front wall may extend in a transverse direction, the transverse direction being transverse to the distal-proximal direction.

The circumferential wall may have a cylindrical or circular-cylindrical outer and/or inner surface. The circumferential wall may comprise or be a circumferentially extending cylindrical wall.

The distal front wall may be positioned oppositely from the proximal end of the housing. The distal front wall may be at least partly coinciding with a distal end of the tip part.

The circumferential wall may be a side wall and/or may have a substantially cylindrical shape. The distal front wall and a camera window may be integrally formed or molded in one piece. Additionally or alternatively, a camera window may be integrally formed or molded in one piece with the circumferential wall. The distal front wall and the circumferential wall may form a liquid-tight (except for any potential inlets, outlets, and openings) barrier or border between an exterior of the tip part or the environment and the interior spacing of the tip part. The exterior housing may also accommodate at least part of a working channel for supplying fluid to a working channel opening in the distal front wall or in the circumferential wall and/or for directing tools through the working channel. The tip part and/or exterior housing may comprise a working channel sleeve for insertion of a working channel tube. A working channel tube may extend from the tip part to a handle of the medical insertion vision device, potentially to a port and/or aggregate in the handle for applying suction and/or allowing insertion of a tool or application of a fluid and/or gas into the working channel tube and/or working channel opening.

By integrally forming the circumferential wall and distal front wall, a sealed tip part may be provided. Additionally, assembly of the tip part may be made simpler as fewer parts are required.

The term "integrally formed in one piece" as used herein may involve that two or more parts are integrally molded in one piece with each other, potentially in a multi-component molding process.

One or more printed circuit boards (PCB) may be connected and/or attached to the camera assembly. Additionally or alternatively, the camera assembly may comprise one or more PCBs. One or more of the PCBs may be or comprise a flexible PCB which may alternatively be denoted a flexible printed circuit (FPC). Two or more PCBs may be connected to each other, potentially to form a main PCB. One or more of the PCBs may have at least one electrical component for converting light received by the camera assembly to an image signal. An image signal may be transmitted, potentially via one or more PCBs or FPCs and/or a data and/or signal image cable, from the camera assembly and/or image sensor to a handle PCB in the handle of the medical device. The handle PCB may transmit the data and/or image signal to a display, via wire or wirelessly. The at least one electrical component may convert an image signal from the image sensor to an alternative signal, the alternative signal potentially being more suited to transmission through a cable or wirelessly, potentially with lower noise and loss. The need for conversion of the image signal to an alternative signal may depend on the length, shielding, and thickness of any cables used. The one or more PCBs may comprise one or more capacitors. The one or more PCBs may further comprise one or more attachment areas for attachment and/or soldering of cables and/or components to the PCBs. One or more PCBs may be positioned in the tip part. One or more PCBs may be positioned in the camera compartment and/or in the potting compartment. One or more PCBs may be positioned in a handle of the medical insertion vision device. One or more of the PCBs may supply power to one or more light sources and/or the camera assembly. A power source for supplying power to the one or more PCBs, potentially via a power cable attached to the PCB, may be provided in the handle of the medical insertion vision device. Alternatively, a power source, such as a stationary or portable power source, may be attached to the medical device. The power source may be arranged in a separate device such as dongle as described herein. Additionally or alternatively, power may be provided through the data and/or signal transmission cable.data and/or signal transmission cable and/or a power cable may extend from the camera assembly to a proximal part of the medical device, potentially to a handle of the device. The medical device may be wirelessly connected to the display to transmit the image. The medical device may comprise a dongle for wirelessly transmitting data and/or an image signal to a display. The lens stack may comprise one or more lenses and may be arranged between the image sensor and the distal front wall, potentially between a camera window and the image sensor. Alternatively, the lens stack may be arranged between the image sensor and the circumferential wall, potentially between a camera window and the image sensor. The one or more lenses may be arranged, potentially in a lens stack, in front of the image sensor, potentially so that an optical axis of the lens, potentially of the one or more lenses, align or coincide with an optical axis of the image sensor. A front or distal lens may form a camera window. The plurality of lenses may be spaced apart by at least one spacer, potentially a plurality of spacers.

In an embodiment, the step of sealing the camera compartment comprises applying the sealing material proximally of a sealing surface.

Additionally or alternatively, the sealing material may be applied on the sealing surface. Additionally or alternatively, the sealing material may be applied in a sealing gap. The sealing material may be positioned proximally of the sealing surface.

In an embodiment a sealing surface is substantially formed by the circumferential wall.

The sealing surface may substantially be formed by or be provided as an inner surface of the circumferential wall.

The sealing surface may be partly formed by a part of and/or section and/or surface of a cable and/or PCB. The sealing surface may be a surface of the exterior housing, potentially the circumferential wall. The sealing surface may be partly formed by a compartment wall that extends from the distal front wall of the housing to a proximal end of the camera compartment or further. The compartment wall may form at least a part of an exterior of a working channel. The compartment wall may be an exterior wall of a working channel. The compartment wall may form at least a part of a working channel sleeve. The compartment wall may extend in the distal-proximal direction. The compartment wall may be enclosed by the circumferential wall. The compartment wall may be provided in the interior spacing. The compartment wall may be separate of the circumferential wall. The compartment wall may be formed integrally and in one piece with the distal front wall. The sealing surface may be a circumferential surface. The sealing surface may have a substantially circular, annular, cylindrical, elliptical, oval, polygonal e.g. rectangular, square, pentagonal, hexagonal, heptagonal, octagonal, nonagonal, or decagonal etc. cross-sectional shape.

In an embodiment, the method further comprising the step of inserting a plate-shaped closing element of the tip part into the camera compartment, the closing element substantially covering a cross-sectional area defined by an interior circumferential sealing surface of the camera compartment, wherein sealing of the camera compartment towards the proximal potting compartment of the interior spacing is by means of the closing element and the sealing material.

The step of inserting the closing element may be simultaneous to the step of inserting the camera assembly. The closing element may be a part of the camera assembly.

The closing element may be inserted in the camera compartment to be positioned at a proximal end of the image sensor. When inserted, a proximal surface of the closing element may extend substantially in the transverse direction. When inserted there may be a predetermined sealing gap between the closing element and the sealing surface. In this way a repeatable and reliable sealing may be achieved, which may be particularly advantageous when producing a large quantity of tip parts. Preferably the predetermined sealing gap is as small as small as possible to prevent sealing material from reaching the camera compartment and interfering with image reception of the camera and light transmission from the one or more light sources, whilst allowing easy insertion of the closing element.

Additionally or alternatively, applying the sealing material may involve applying the sealing material on a proximal surface and/or an outer circumferential surface of the closing element.

Additionally or alternatively, the sealing material may be applied between the closing element and the sealing surface. Additionally or alternatively, the sealing material may be applied at a proximal end of the closing element, potentially to a proximal surface thereof. The sealing material may be applied such that a sealing gap between the sealing surface and closing element is covered by the sealing material, thereby sealing the sealing gap. The sealing material may be applied by cannula.

The data and/or signal transmission cable and/or power cable may be connected to the one or more PCBs. The data and/or signal transmission cable and/or power cable may be a part and/or form at least a part of a PCB, potentially a flexible PCB. The one or more PCBs may supply power to the camera assembly and/or light sources. The one or more PCBs may transmit data and/or an image signal from the camera assembly and/or image sensor. The data and/or signal transmission cable and/or power cable may extend adjacent to the closing element potentially abutting the closing element and/or being pressed against the interior sealing surface by the closing element. The data and/or signal transmission cable and/or power cable may be pressed against the interior sealing surface by the closing element such that the data and/or signal transmission cable and/or power cable deforms, potentially to a shape complementing the sealing surface and/or closing element. The data and/or signal transmission cable and/or power cable of the camera assembly may extend through the closing element towards a proximal end of the medical insertion vision device. The data and/or signal transmission cable and/or power cable may be connected to the image sensor, potentially a proximal surface of the image sensor. The data and/or signal transmission cable and/or power cable may be connected to the image sensor via the one or more PCBs. The data and/or signal transmission cable and/or power cable may extend through a sealed cable sheath. The cable sheath may be sealed to the proximal end of the closing element and/or camera assembly. The cable sheath may be in the form of a sleeve and/or tube.

Alternatively, the one or more PCBs may extend adjacent to the closing element potentially abutting the closing element and/or being pressed against the interior sealing surface by the closing element. The one or more PCBs may be pressed against the interior sealing surface by the closing element such that the one or more PCBs deform, potentially to a shape complementing the sealing surface and/or closing element. For this purpose, the PCB(s) being pressed against the sealing surface by the closing element are preferably FPC(s) to facilitate deformation. The one or more PCBs may extend through the closing element towards a proximal end of the medical insertion vision device. The one or more PCBs may be connected to the image sensor, potentially a proximal surface of the image sensor.

A further embodiment concerns the method, wherein together with the step of inserting the camera assembly one or more light guides are also inserted into the camera compartment.

By inserting the light guides into the sealed camera compartment it may be prevented that potting material reaches the light guides and interferes with the transmission of light therethrough.

The light guides may be formed integrally and in one piece with the closing element. The term "integrally formed in one piece" as used herein may involve that two or more parts are integrally molded in one piece with each other, potentially in a multi-component molding process as disclosed herein. The one or more light guides may be inserted into the camera compartment to a final position of the manufactured tip part. The light guides may extend to the distal front wall and/or a camera window of the tip part, potentially to be positioned directly proximally of and/or to abut a respective light guide window and/or light guide of the distal front wall and/or camera window. Alternatively, the light guides may extend to the circumferential wall and/or a camera window of the tip part, potentially to be positioned directly proximally of and/or to abut a respective light guide window and/or light guide of the circumferential wall and/or camera window. The distal front wall and/or circumferential wall may comprise one or more light guides. The tip part, potentially a main printed circuit board (PCB) of the tip part may comprise one or more light sources such as LEDs. The one or more light sources may be positioned to abut and/or be attached to a proximal surface of the closing element. The method may further comprise the step of positioning one or more light sources to abut the closing element prior to inserting the closing element. Additionally or alternatively, the method may comprise the step of attaching one or more light sources to the closing element prior to inserting the closing element. The one or more light sources may be attached to the closing element by an adhesive, potentially a transparent adhesive. The method may comprise the step of positioning one or more light sources to abut the closing element subsequent to inserting the closing element. The method may comprise the step of attaching one or more light sources to the closing element subsequent to inserting the closing element. The closing element may comprise one or more recesses for positioning of the one or more light sources. The one or more recesses may be positioned on a proximal side and/or a proximal surface of the closing element. The one or more recesses and/or the one or more light sources may be positioned directly proximally of one or more light guides. The one or more recesses may be formed integrally and in one piece with one or more light guides and/or the closing element.

At least a part of the main PCB and/or a majority and/or an entirety of the main PCB may be positioned outside of the camera compartment. The main PCB may be positioned inside the interior spacing. The data and/or signal transmission cable and/or power cable may be connected to the main PCB.

The method may further comprise the step of curing, potentially immediately curing, the sealing material subsequent to application thereof.

The closing element may substantially cover a cross-sectional area of the camera compartment at the sealing surface. The closing element may have a cross-sectional shape that is complementary to the shape of the cross-sectional area defined by the sealing surface. There may be an air-sealing gap between the closing element and the sealing surface, potentially before the sealing material is applied. The air-sealing gap may extend between an exterior circumferential surface of the closing element and the sealing surface.

The closing element may have a cross-sectional shape that is complementary to the circumferential sealing surface. The closing element may be substantially crescent-shaped. The closing element may be substantially disc-shaped.

The closing element may be positioned proximally of the image sensor and/or the lens stack. The closing element may be attached to the image sensor, potentially to a proximal end of the image sensor. The closing element may be attached by means of an adhesive and/or sealing material. The closing element may be positioned within the camera compartment. The closing element may be positioned distally of a PCB of the camera assembly.

If the tip part comprises a working channel and/or a working channel sleeve, the closing element may at least partly enclose and/or abut the working channel and/or a working channel sleeve. An exterior circumferential surface of the closing element may at least partly enclose and/or abut the working channel and/or working channel sleeve.

At least a portion of the closing element may abut the sealing surface.

The tip part may comprise a camera window positioned in or forming part of the distal front wall and/or the circumferential wall. The camera window and/or distal front wall may be formed integrally and/or in one piece with the circumferential wall. The camera window may have different shapes, such as circular, crescent, half-moon shaped etc. The camera window may comprise a plurality of window parts.

Additionally or alternatively, the tip part may comprise a working channel opening and a camera window in the circumferential wall. Such a configuration may for example be for a duodenoscope. The tip part may be a tip part for forming at least a part of a tip of a duodenoscope. The medical insertion vision device may be a duodenoscope.

Another embodiment concerns the method, wherein parts of the sealed camera compartment not occupied by components of the tip part are air-filled.

The components may be one or more PCBs, light guides, light sources, the closing element, the camera assembly including the lens stack and image sensor etc.

Air may be understood as a gas such as the atmospheric air. The term "parts of the sealed camera compartment not occupied by components" may be understood as "volumes" or "spacings" of the sealed camera compartment not occupied by components. The term "not occupied by" may be understood as "not filled by" or "not taken up by" i.e. the parts and/or spacings and/or volumes of the camera compartment may be empty and void of components of the tip part. Alternatively, the parts of the sealed camera compartment not occupied by components may be filled with a biocompatible inert gas e.g. nitrogen.

An element or component "positioned within the camera compartment" in the context of this disclosure may be understood as or may involve that such element is positioned inside the camera compartment between the proximal end and a distal end of the camera compartment.

The sealing material may be a liquid material at application and may include an adhesive. The sealing material may have a higher viscosity than the potting material. The sealing material may have a higher viscosity at application than the potting material. The sealing material and/or the potting material may be an adhesive. The sealing material may have a viscosity equal to or higher than 800, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000, 3100 or 3200 cP measured at 25+/−0.2 degrees Celsius with a Brookfield R/S-CPS+ Rheometer (or according to test 6.3 in the standard DS/EN 12092:2001). Followingly, expressed in Pascal-seconds (Pa*s) the sealing material may have a viscosity equal to or higher than 0.8, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1 or 3.2 Pa*S measured at 25+/−0.2 degrees Celsius with a Brookfield R/S-CPS+ Rheometer (or according to test 6.3 in the standard DS/EN 12092:2001). This may provide good control of the application and spread of the adhesive during and/or after application and may enable the adhesive to be cured at a desired position. The sealing material may have a viscosity chosen from the following group of ranges of viscosity: between 800-3200 cP (0.8-3.2 Pa*s), 950-1300 cP (0.95-1.3 Pa*s), or 2400-3200 cP (2.4-3.2 Pa*s) measured at 25+/−0.2 degrees Celsius with a Brookfield R/S-CPS+ Rheometer (or according to test 6.3 in the standard DS/EN 12092:2001). The sealing material may be curable by heat, light, and/or chemical reaction. The sealing material may be curable by ultra-violet (UV) light and/or LED light. The sealing material may be an acrylated urethane. The acrylated urethane may have a viscosity as described above. For example, it may have a viscosity of 1000 cP (1 Pa*s) measured at 25+/−0.2 degrees Celsius with a Brookfield R/S-CPS+ Rheometer (or according to test 6.3 in the standard DS/EN 12092:2001).

The potting material may be a thermosetting plastic, a silicone rubber, an epoxy resin, or a combination thereof. The potting material may be a liquid material at application and may include an adhesive. The potting material may be an adhesive. The potting material may have a lower viscosity than the sealing material. The potting material may have lower viscosity at application than the sealing material. The potting material may have a viscosity of equal to or less than 800, 750, 700, 650, 600, 550, 500, 450, 400, 350, 300, 250, 200, 150, 120, 100, 75, or 50 cP measured at 25+/−0.2 degrees Celsius with a Brookfield R/S-CPS+ Rheometer (or according to test 6.3 in the standard DS/EN 12092:2001) or measured at 25+/−0.2 degrees Celsius, and 20 rpm using a Brookfield RVDV-II+ (or according to test 6.2 in the standard DS/EN 12092:2001). Followingly, expressed in Pascal-seconds (Pa*s), the potting material may have a viscosity of equal to or less than 0.8, 0.75, 0.7, 0.65, 0.6, 0.55, 0.5, 0.45, 0.4, 0.35, 0.3, 0.25, 0.2, 0.15, 0.12, 0.1, 0.075, or 0.05 Pa*s measured at 25+/−0.2 degrees Celsius with a Brookfield R/S-CPS+ Rheometer (or according to test 6.3 in the standard DS/EN 12092:2001) or measured at 25+/−0.2 degrees Celsius, and 20 rpm using a Brookfield RVDV-II+ (or according to test 6.2 in the standard DS/EN 12092:2001). The potting material may have a viscosity between 50-800 cP (0.05-0.8 Pa*s) measured at 25+/−0.2 degrees Celsius with a Brookfield R/S-CPS+ Rheometer (or according to test 6.3 in the standard DS/EN 12092:2001) or measured at 25+/−0.2 degrees Celsius, and 20 rpm using a Brookfield RVDV-II+ (or according to test 6.2 in the standard DS/EN 12092:2001). The potting material may have a viscosity between 100-200 cP (0.1-0.2 Pa*s) measured at 25+/−0.2 degrees Celsius, and 20 rpm using a Brookfield RVDV-II+ (or according to test 6.2 in the standard DS/EN 12092:2001). The potting material may have a viscosity between 120-200 cP (0.12-0.2 Pa*s) measured at 25+/−0.2 degrees Celsius with a Brookfield R/S-CPS+ Rheometer (or according to test 6.3 in the standard DS/EN 12092:2001). In this way the potting material may have good flow properties and be able to reach and substantially completely fill the potting compartment.

The potting material may be curable by heat, light, and/or chemical reaction. The potting material may be curable by UV light and/or LED light. The potting material may be cured after application. The potting material may be an acrylated urethane. It may have a viscosity as described above. For example it may have a viscosity of 75 cP or 150 cP (0.075 or 0.15 Pa*s) measured at 25+/−0.2 degrees Celsius with a Brookfield R/S-CPS+ Rheometer (or according to test 6.3 in the standard DS/EN 12092:2001) or measured at 25+/−0.2 degrees Celsius, and 20 rpm using a Brookfield RVDV-II+(or according to test 6.2 in the standard DS/EN 12092:2001).

The potting material may be the same material as the sealing material. The potting material may be applied at a different viscosity than the sealing material. The potting material may be applied at a different temperature than the sealing material. The potting material may comprise the sealing material and may optionally include a dilutent.

A second aspect of this disclosure relates to a tip part for forming at least part of a tip of a medical insertion vision device, the tip part comprising: an exterior housing of the tip part having an open proximal end for connection to other parts of the device, the housing further having a distal front wall and a circumferential wall, the circumferential wall extending from the distal front wall to the proximal end of the housing, the distal front wall and the circumferential wall enclosing an interior spacing of the tip part; and a camera assembly positioned in a distal, air-filled camera compartment of the interior spacing, the camera assembly comprising an image sensor and a lens stack, the lens stack being positioned distally of the image sensor, whereby the image sensor can provide an image from an object to be investigated; wherein the air-filled camera compartment is sealed towards a proximal potting compartment of the interior spacing by means of a sealing material; wherein after a potting material has been potted into the potting compartment, the potting material does not extend farther distally than to a proximal end of the image sensor.

In this way, it may be prevented that potting material interferes with light transmission to and/or through the image sensor or lens stack.

All embodiments, options, and comments above regarding the methods and medical insertion vision devices of this disclosure, also apply to the tip part of this disclosure.

In a development of the previous embodiment, the air-filled camera compartment is sealed towards the proximal potting compartment by means of the sealing material and a plate-shaped closing element covering a cross-sectional area defined by an interior circumferential sealing surface of the camera compartment, and wherein the sealing material is provided proximally of the sealing surface of the camera compartment.

In an embodiment, one or more light guides are positioned within the camera compartment.

At least two light guides may be positioned within the camera compartment. A light guide may be positioned on each side of the image sensor and/or lens stack. The one or more light guides may extend from the closing element to the distal front wall, potentially to a proximal surface of the distal front wall or of an interior surface of the circumferential wall. The light guides may be positioned with a distance to each other in the transverse direction. The distance may be equal to or more than a largest extent of the image sensor in the transverse direction. The one or more light guides may be positioned adjacent and/or in close proximity to the circumferential wall. The one or more light guides may be positioned a distance equal to or less than a largest extent in the transverse direction of a light guide from the circumferential wall. One or more light guides may be positioned at, in the transverse direction, opposite sides of the tip part.

In a development of the previous embodiment, the one or more light guides are formed integrally and in one piece with the closing element.

In this way potential leaks at a sealing between the light guides and the closing element may be prevented. Furthermore, it may enable the light guides to be positioned in the camera compartment simultaneously with the insertion of the closing element.

In an embodiment, the sealing surface is substantially formed by the circumferential wall.

In an embodiment, one or more light sources are positioned to abut and/or are attached to the closing element, the one or more light sources potentially being positioned on a proximal surface of the closing element.

This may prevent potting and/or sealing material from interfering with the light emitted by the light sources potentially by flowing onto and/or in front of the one or more light sources, particularly when the light sources are attached to the closing element prior to application of the sealing material and/or potting material.

The one or more light sources may be positioned on the proximal surface of the closing element so as to emit light towards and/or into the one or more light guides. At least one light source may be positioned on the proximal surface of the closing element so as to emit light towards and/or into each of the one or more light guides. The one or more light sources may be positioned directly proximally of the one or more light guides. At least two light sources may be attached to the closing element. The one or more light sources may be LEDs and/or optical fibers. A light source may be positioned on each side of the image sensor and/or lens stack. When two or more light sources are attached to the closing element, the light sources may be positioned with a distance to each other in the transverse direction. The distance may be equal to or more than a largest extent of the image sensor in the transverse direction. The one or more light sources may be positioned adjacent and/or in close proximity to the circumferential wall. The one or more light sources may be positioned a distance equal to or less than a largest extent in the transverse direction of a light guide from the circumferential wall. One or more light sources may be positioned at, in the transverse direction, opposite sides of the tip part.

In an embodiment, the exterior housing comprises at least a part of a working channel, the working channel having an opening in the distal front wall of the housing. The part of the working channel may be a distal part of the working channel. Alternatively, the working channel has an opening in the circumferential wall of the housing.

The working channel may allow liquid to be removed from a body cavity and/or allow insertion of surgical instruments or the like into the body cavity. The working channel may be provided as a channel extending from a proximal end of the medical insertion vision device to a distal end of the device to guide a tool and/or to provide suction. A connector and/or a connecting portion may be provided at the proximal end of the medical insertion vision device to allow insertion of a tool into the working channel and/or to allow suction to be applied to the working channel. In some embodiments, the working channel comprises a built-in or integrated tool at or in the tip part. Such a tool may be suitable for grabbing, taking, and/or holding elements in a part of a patient, in which the medical insertion vision device tip part is arranged during use. Alternatively, the working channel may be provided in a second lumen separate of the tip part.

The working channel may be at least partly housed in the exterior housing of the tip part. The working channel may, alternatively, be entirely housed in the housing. The working channel may be positioned in a bottom part of the tip part. The working channel and/or working channel opening may be positioned below the camera compartment. The working channel and/or working channel opening may be positioned below a camera window and/or the light guides and/or the closing element and/or the camera assembly and/or the one or more PCBs. The closing element may be shaped to at least partly surround and/or abut the working channel. The tip part may comprise a working channel holder for holding and/or surround at least a distal part of the working channel. The working channel holder may comprise and/or constitute a part of the working channel and may extend into and/or comprise the working channel opening. A distal part of the working channel holder may terminate into the working channel opening.

All embodiments, options, and comments above regarding the tip part and medical insertion vision device of this disclosure also apply to the methods of this disclosure.

In a third aspect this disclosure relates to a medical insertion vision device comprising a tip part manufactured according the first aspect or comprising a tip part according the second aspect.

The medical insertion vision device may be a disposable medical insertion vision device. The medical insertion vision device may include one or more features as described herein in the above, including the features described in the above introduction to this description, and in connection with the description of the methods and tip parts according to the present disclosure.

The medical insertion vision device in particular an endoscope, may comprise an elongated insertion tube with a handle at the proximal end. The tip part may be positioned at the distal end of the elongated insertion tube. The tip part may further be attached to a bending section positioned between the tip part and the elongated insertion tube. The bending section may be configured to be articulated to maneuver the medical insertion vision device inside a body cavity. The device may comprise one or more steering wires for steering at least the tip part of the device potentially in an up/down and/or left/right direction. The device may comprise a control arrangement, potentially forming part of a handle of the device, for tensioning or slackening the steering wire(s) to steer at least the tip part of the device. In some embodiments of the medical insertion vision device, the medical insertion vision device further comprises a distal tip or tip part that comprises a bending section connected to the steering wire(s) so that the control mechanics can activate a bending operation of the bending section via the steering wire(s).

The insertion tube may be attached to the tip part or bending section by an adhesive and/or crimps. Similarly, if present, the bending section may be attached to the insertion tube and/or tip part by an adhesive and/or crimps.

In an embodiment, the medical insertion vision device is an endoscope.

In an embodiment, the medical insertion vision device is a catheter, such as an endotracheal tube, in particular a single lumen or dual lumen endotracheal tube or a feeding probe.

In an embodiment, the medical insertion vision device is a medical tool comprising a camera.

A fourth aspect of this disclosure relates to a system comprising: a medical insertion vision device according to the third aspect; and a display for displaying an image provided by the camera assembly of the medical insertion vision device.

In the above, the tip part has mainly been described in application in an endoscope, however, the tip part is equally suitable for application in other medical devices such as catheters e.g. endotracheal tubes, in particular single lumen or dual lumen endotracheal tubes, or feeding probes, or medical tools carrying a camera.

The tip part may be for forming at least a part of a tip of a catheter or a feeding probe or a medical tool. The tip part may be for forming at least a part of tip of a camera lumen, potentially a camera lumen of a catheter. The camera lumen may be a dedicated camera lumen. The dedicated camera lumen may be separate of a second lumen, such as for example a working channel lumen. A working channel lumen may also be denoted a catheter lumen.

The tip of the medical insertion vision device may be a tip of a camera lumen, potentially a separate camera lumen, for example in a dual lumen tube. The dual lumen tube may e.g. be for a catheter and/or endotracheal tube. A camera lumen, potentially a distal most part of the camera lumen, may be positioned proximally of a second lumen, potentially proximally of a distalmost part of the second lumen. The camera lumen may be positioned in a tube wall of a single or dual lumen tube. The camera lumen may extend along an exterior of a working channel lumen. The camera lumen may be positioned externally of a working channel lumen.

The open proximal end of the exterior housing of the tip part may be closed by a cap element. The cap element may extend transversely at the proximal end of the circumferential wall. Data and/or power cables may extend through the cap element, potentially through a camera lumen, towards the proximal end of the device.

A catheter may be for cardiovascular, urological, gastrointestinal, neurovascular, and ophthalmic applications. A catheter may allow drainage and/or administration of fluids or gases, insertion of tools such as surgical instruments. A catheter may comprise one or more fluid and/or gas channels and/or one or more working channels. A catheter may comprise a needle or cannula for drainage and/or administration of fluids or gases. A catheter may comprise a filter for filtering of fluids and/or gases.

The catheter may comprise a first inflatable cuff, potentially positioned on a first lumen of the catheter. The catheter may comprise a second inflatable cuff, potentially positioned on the first or second lumen. Additionally or alternatively, the catheter may comprise an inflatable cuff surrounding both the first and the second lumen. Additionally or alternatively, the first and/or second inflatable cuff may surround both the first and second lumen.

The one or more light guides may extend from the closing element to the front wall, potentially to an interior surface of the circumferential wall and/or a side wall.

A catheter or endoscope may comprise and/or substantially consist of one more of the following materials: polymers such as silicone rubber, latex rubber, nylon, polyvinyl chloride (PVC), polyethylene terephthalate (PET), latex, or thermoplastic elastomers.

A person skilled in the art will appreciate that any one or more of the above aspects of this disclosure and embodiments thereof may be combined with any one or more of the other aspects and embodiments thereof.

BRIEF DESCRIPTION OF THE FIGURES

In the following, non-limiting exemplary embodiments will be described in greater detail with reference to the drawings. The figures show one way of implementing the present disclosure and are not to be construed as being limiting to other possible embodiments falling within the scope of the attached claim set.

FIGS. 5a and 5b show cross-sections of variations of the embodiment of the tip part of FIG. 5;

FIG. 5c shows a cross-section of another variation of the embodiment of the tip part of FIG. 5;

DETAILED DESCRIPTION

Figure 1:
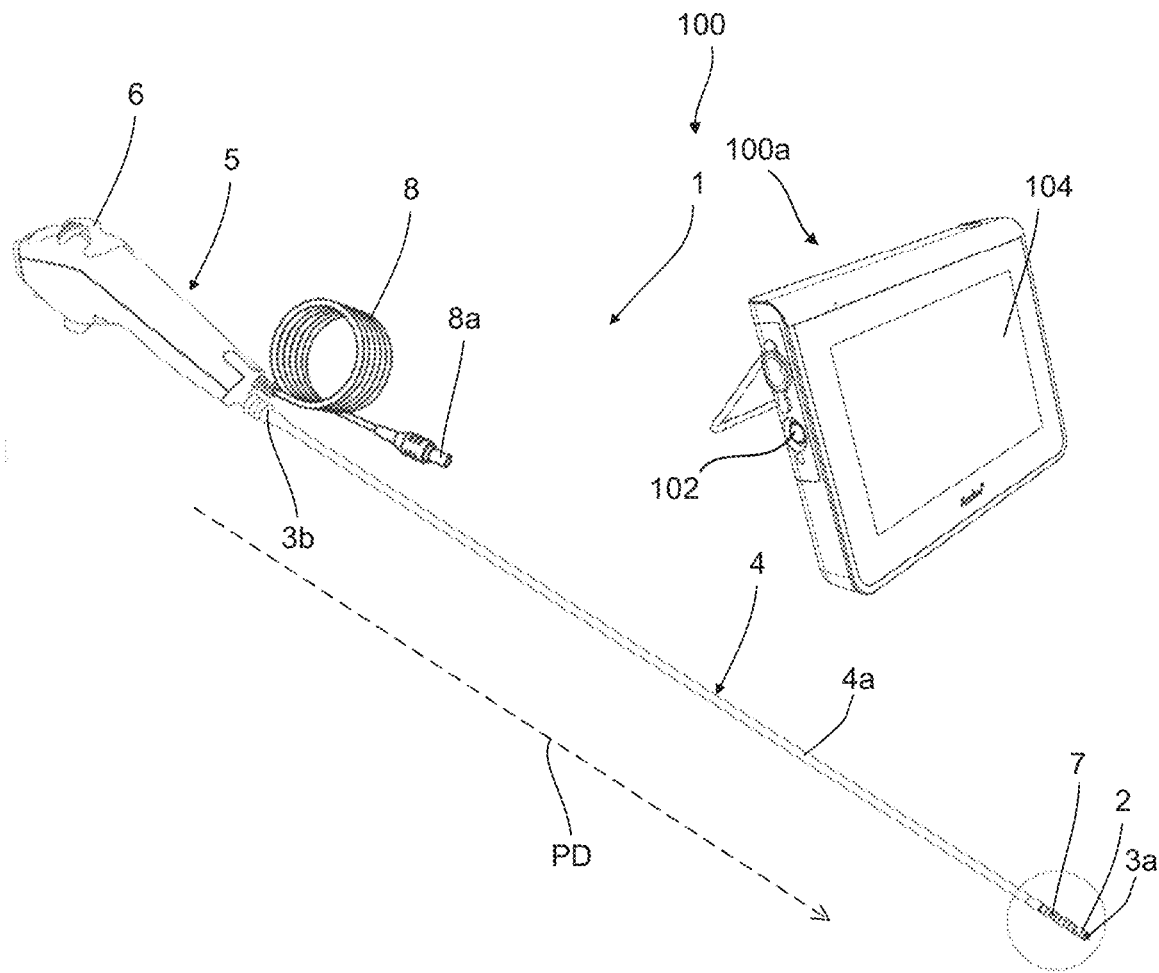
FIG. 1 shows an embodiment of a system comprising an embodiment of a medical insertion vision device in the form of a disposable insertion endoscope and a monitor device according the present disclosure.
Figure 2:
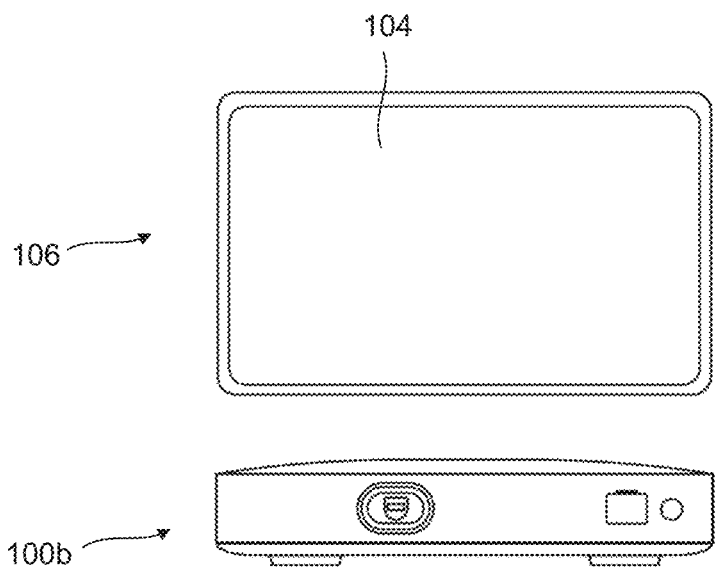
FIG. 2 shows a variation of a monitor device.

FIG. 1 shows a visualization system 100 including a disposable or single-use medical insertion vision device, here exemplified by a disposable insertion endoscope 1, and a monitor device 100a having a connection port 102 and a display screen 104. Example endoscopes include ureteroscopes, ENT scopes, duodenoscopes, and any other endoscope used for any other medical purpose. Alternatively, the medical insertion vision device could be a catheter with a built-in camera unit, such as a single lumen or dual lumen endotracheal tube, or a feeding probe with a built-in camera, or a medical tool comprising a camera. The single-use medical insertion vision device can be any device that can be inserted into a patient and has a camera in a distal tip as described below. In a variation of the visualization system 100 shown in FIG. 2, a monitor device 100b is shown that does not include an integrated display screen 104. A display device 106 including a display screen 104 is provided, which device is communicatively connectable with the monitor device 100b and, optionally, also with the monitor device 100a.

The endoscope 1 includes a distal tip with a tip part 2, the tip part 2 being an embodiment of the tip part according to the second aspect of the present disclosure. The tip part is manufactured according to the methods of the present disclosure.

The tip part 2 is positioned at a distal end 3a of an elongated insertion cord, or tube, 4 of the endoscope 1. The insertion tube 4 is at a proximal end 3b connected to an endoscope handle 5, which includes a control arrangement 6 for controlling bending of a bending section 7 positioned near, or in other embodiments as a not shown part of, the tip part 2. In the shown embodiment, the bending section 7 is positioned between the tip part 2 and the insertion tube 4. The bending section 7 is configured to be articulated to manoeuvre the endoscope 1 inside a body cavity. The handle 5 further comprises a cable 8 with a connector 8a for connecting to the monitor device 100a, 100b for displaying an image provided by the camera assembly of the endoscope 1.

The connector 11 is insertable in a monitor connector 102 of the monitor device 100a, 100b. The monitor device 100a, 100b can be connected, wirelessly or via a cable, with the display device 104. In the case of the monitor device 100a, the connection can be to an additional display device 104 that is not integrated with the monitor device 100a. The medical insertion vision device and the monitor device 100a, 100b can also include transceivers to communicate images and configuration data between them wirelessly, for example via a wireless HDMI protocol. A dongle may be provided including a wireless transceiver. The dongle may be removably connectable to the medical insertion vision device so that it can be removed prior to disposal of it. A dongle can also be provided to connect with the monitor device.

The handle 5 can be considered a position interface between user and the cord or insertion tube 4. The function of the handle is for the operator of the medical insertion vision device to grasp the handle to position the insertion tube 4 in the appropriate place. The handle also functions to provide control knobs, actuators, ports, etc., for controlling the position of the tip part and instruments guided through the insertion tube. Alternatively, a different position interface can be provided that is connected to the insertion tube 4 and removably attaches to a robotic arm. The insertion tube, or insertion cord, 4 thus extends from the robotic arm and the medical insertion vision device remains detachable from the robotic arm and disposable. The tip part is the same regardless of the position interface used. The robotic arm responds to signals, including voice commands, from the operator to rotate, translate, and otherwise position the proximal end of the insertion cord, as an operator would do manually. The proximal ends of the pull-wires 25d would then be connected to an actuator operable to translate the wires. Example actuators include single axis actuators such as linear motion actuators, in some examples including a threaded rod coupled to a threaded nut portion rotatable by a motor. In other examples a slider type actuator may be used. The motor is controlled in the same manner as the robotic arm, via signals initiated by the operator. Rotation clockwise or counterclockwise translates the wire to and fro.

Figure 3:
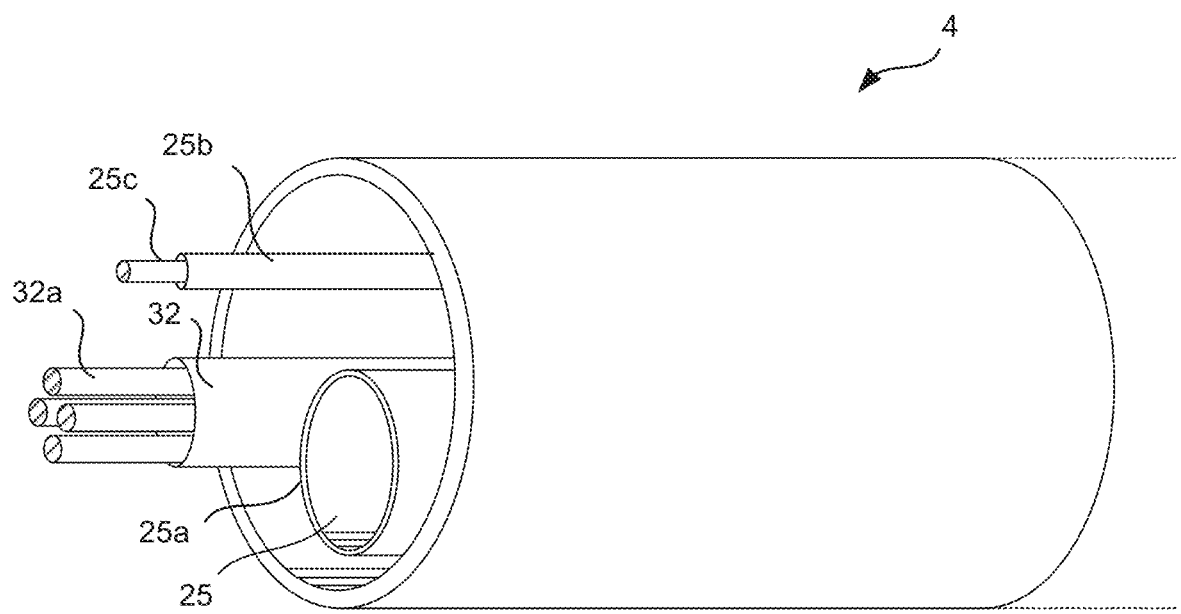
FIG. 3 shows a proximal view of the insertion tube.

FIG. 3 shows a proximal end of a portion of the insertion tube 4 illustrating the working channel 25, a tube 25a providing the working channel portion between the distal tip and the position interface, a cable sheath 32 including therein a plurality of cables, or wires, 32a, and a sheath 25b of a Bowden cable comprising a pull-wire 25c. One or more pull-wires may be provided between the handle and the distal tip. Translation of the pull-wires articulates the bending section and repositions/reorients a camera at the distal tip, as is known in the art.

Figure 4:
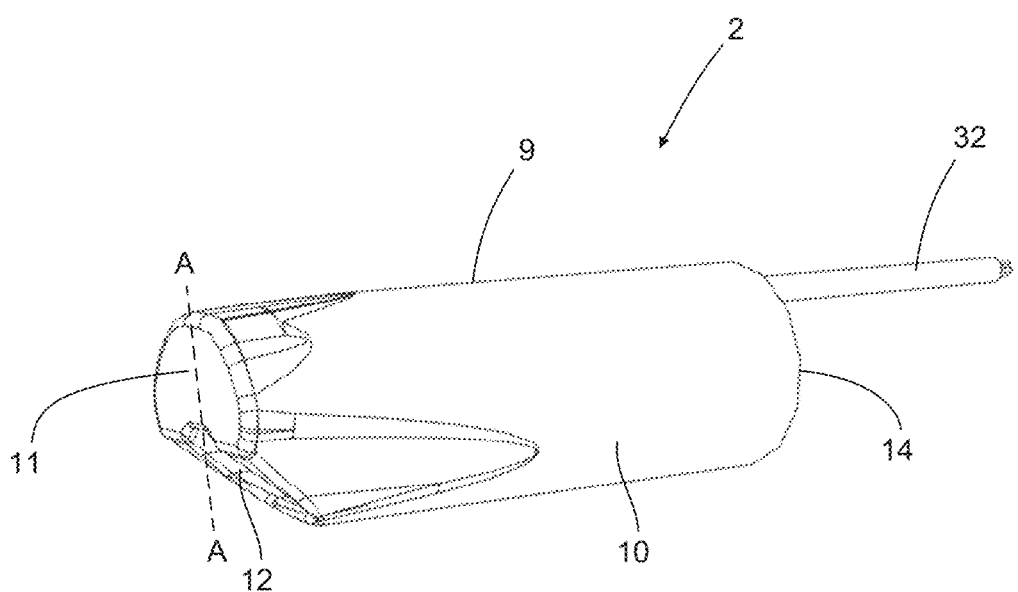
FIG. 4 shows a perspective side view of the tip part of the endoscope in FIG. 1.

FIG. 4 shows a perspective side view of the tip part 2 of the endoscope 1 in FIG. 1. The tip part has an exterior housing 9 with a cylindrical circumferential wall 10 and a distal front wall 11, the circumferential wall 10 extending in the proximal-distal direction PD from the distal front wall 11 to an open proximal end 14 of the housing 9, the open proximal end 14 being for connection to other parts of the device such as the insertion tube 4, outer sheath 4a, and the bending section 7. The insertion tube 4 and the bending section 7 are attached by adhesive and/or crimps and/or press-fit. A cable sheath 32 protecting data, power, and image signal cables extending from a PCB in the tip part 2 towards the proximal end of the endoscope 1 is also seen. Alternatively, when the tip part is implemented for instance in a catheter, the tip part may be a tip part of a dedicated camera lumen, which is separate of a second lumen, such as for example a working channel lumen (which may also be denoted a catheter lumen). In this case, the open proximal end of the tip part may be closed by cap element through which data and power cables can extend through the camera lumen towards a proximal end of the device.

Figure 5:
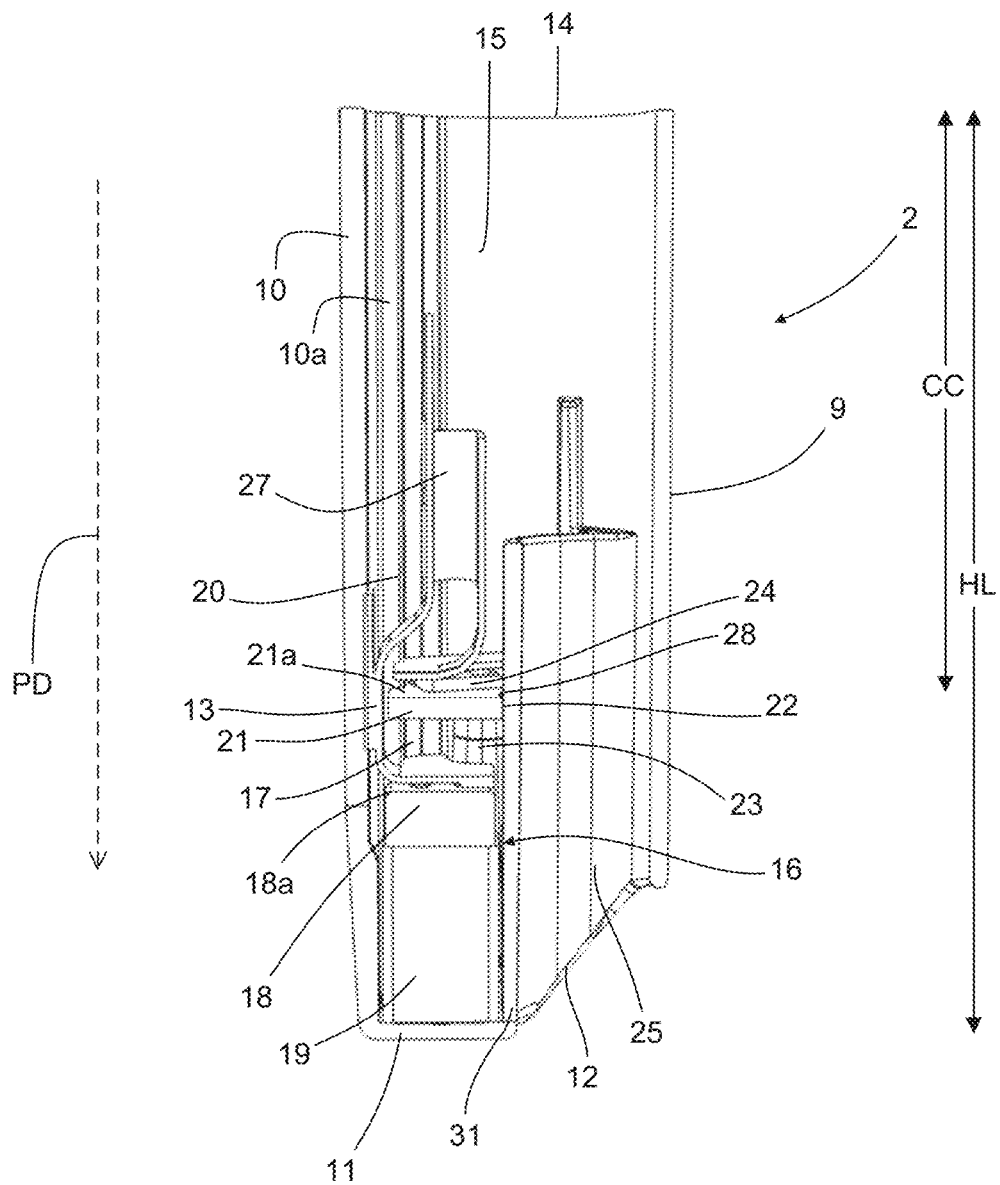
FIG. 5 shows a cross-section of the tip part along line A-A in FIG. 4.

FIG. 5 shows a cross-section of the tip part along line A-A in FIG. 4. It can be seen that the distal front wall 11 and the circumferential wall 10 enclose an interior spacing 15. A camera assembly 16 is positioned in a distal, camera compartment 17 of the interior spacing 15. The interior spacing 15 is a volume enclosed by the distal front wall 11 and the circumferential wall 10. The camera compartment 17 is a distal volume of the interior spacing 15 and may comprise the distal-most half of the exterior housing 9 and or interior spacing 15. A distal end 28 of a potting compartment 20 abuts a sealing material 17a that seals the camera compartment 20 of the interior spacing 15, thus it can be said that the camera compartment extends distally of the seal and the potting compartment begins at the seal. These labels are provided to facilitate illustration of the concepts described herein.

A working channel 25 is shown. The working channel is provided by a circumferential internal wall adapted to receive, at a proximal end thereof, a tube 25a forming the remaining part of the working channel 25, as discussed with reference to FIG. 3. However, not all medical insertion vision devices include working channels, therefore the working channel can be omitted.

The camera assembly 16 comprises an image sensor 18 and a lens stack 19, the lens stack 19 being positioned distally of the image sensor 18, whereby the image sensor 18 can provide an image from an object to be investigated. The image sensor 18 has a proximal end 18a. The camera compartment 17 is sealed forward of the potting compartment 20 by means of the sealing material 17a (see FIGS. 5a and 5b). A potting material 20a (see FIGS. 5a and 5b) has been potted into the potting compartment 20, the potting material not extending farther distally than the seal formed by the sealing material 17a. It is desirable to prevent that potting material interferes with light transmission to the image sensor 18 or lens stack 19. It is also desirable that potting material does not contact the light guides (described below).

A plate-shaped closing element 21 substantially covers a cross-sectional area defined by an interior circumferential sealing surface 22 of the camera compartment 17, where the sealing material is provided proximally of the sealing surface 22 of the camera compartment 17, on a proximal surface 21a of the closing element 21. A gap is formed between the sealing surface 22 and the periphery of the closing element 21. The gap does not necessarily have the same width along the periphery of the closing element 21 and the gap can vary with the dimensions of the tip part since it might be more difficult to position the closing element 21 in very small tip parts with a tight gap. Therefore, the viscosity and application temperature of the sealing material 17a and the gap are chosen to achieve a desirable amount of penetration of the sealing material 17a into the gap to provide a seal sufficient to prevent the potting material 20a from passing distally therethrough.

FIG. 5a shows a schematic diagram of a bisected exterior housing 9 of a tip part 2 adapted for use in medical insertion vision devices, such as endoscopes without working channels, and endotracheal tubes, as discussed with reference to FIGS. 10 and 11. The schematic diagram is not drawn to scale, and some components are not shown, to better illustrate certain aspects of the tip part. The tip part in FIG. 5a is the same in respects relevant to the camera and potting compartments as the tip part in FIG. 5, the difference between them being the absence of a working channel. The camera compartment 17 extends forward, or distally, of the sealing material 17a, which extends between the closing element 21 and the circumferential wall 10 and/or the FCB 13, a portion of which passes between the closing element 21 and the circumferential wall 10. The volume of the camera compartment 17 not filled by the camera assembly 16, the light guides 23, FCB 13, and any other components may be referred to as free-space. The free-space is substantially air-filled. In particular, air surrounds the light guides 23. Of course some adhesive material may be allowed but potting material is excluded. The exposed surfaces of LEDs 24 (except the emitting surfaces) may be surrounded by the potting material 20a. The potting material 20a fills at least some of the free-space of the potting compartment, particularly the distal space of the potting compartment 20, to secure the camera assembly in place. The potting material 20a may fill, beginning with the distal end of the potting compartment, at least 30, 40, 50, 60, 70% or more of the potting compartment. A distal segment of the bending section may be secured to the proximal end of the exterior housing 9 and this may require insertion of a portion of the distal segment into the spacing, as is known in the art.

FIG. 5b shows another example of sealing material penetration. The structural components are the same as in FIG. 5a, but the amount of sealing material 17a penetrating the gap is greater and some sealing material 17a extends into the camera compartment, potentially up to the proximal end 18a of the image sensor 18 around the FPC 13. This extra amount of sealing material 17a is located around FPC 13 and not the light guides 23. Although not preferable, it is permissible that sealing material 17a contacts the light guides 23.

FIG. 5c shows a further example of a tip part with the structural components as in FIG. 5a, except that the closing element is omitted and the LEDs 24 are brought forward of the FPC 13, which provides power to the LEDs 24 and the image sensor 18 and a communication path for the images. An clear adhesive may be used to bond the emitting surface of the LEDs to the light guides 23. A support member (not shown) may be provided to aid in insertion of the camera assembly, which support member may have a flat surface abutting the FPC 13. As in FIGS. 5a and 5b, the sealing material 17a extends up to the proximal end 18a of the image sensor 18 around the FPC 13.

Figure 6:
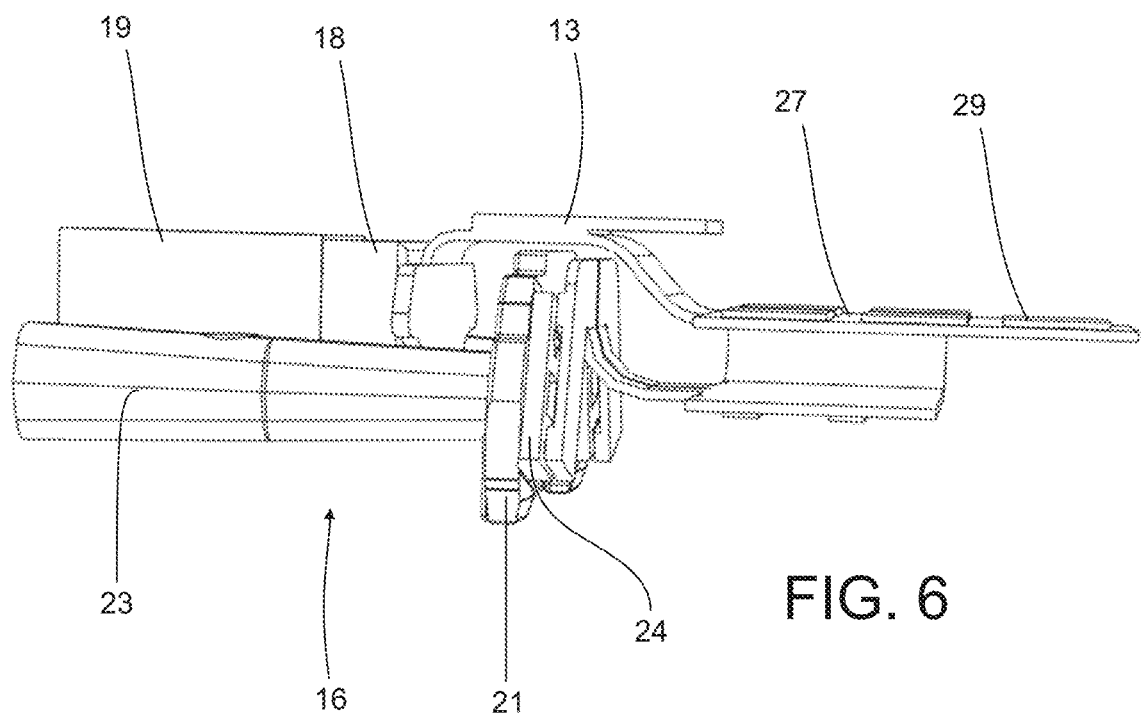
FIG. 6 shows a perspective side view of the closing element and camera assembly of FIG. 5.
Figure 7:
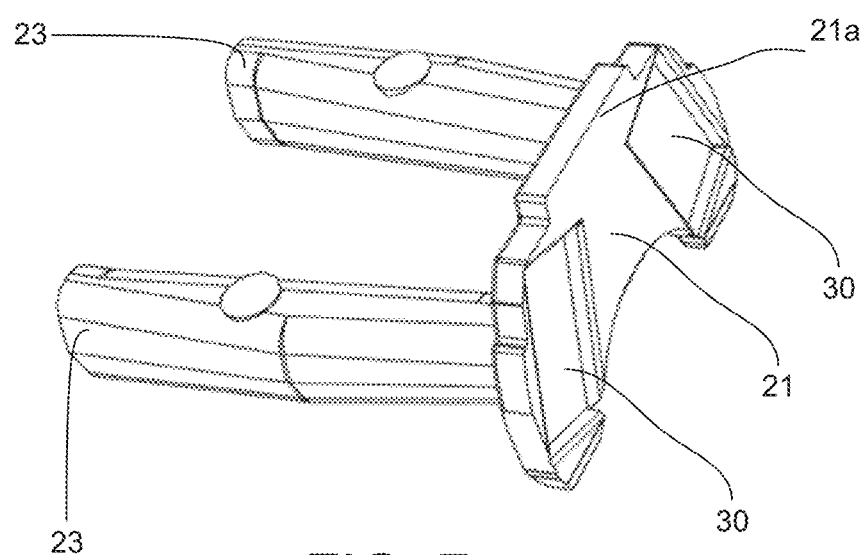
FIG. 7 shows a perspective side view of the closing element of FIG. 6.
Figure 8:
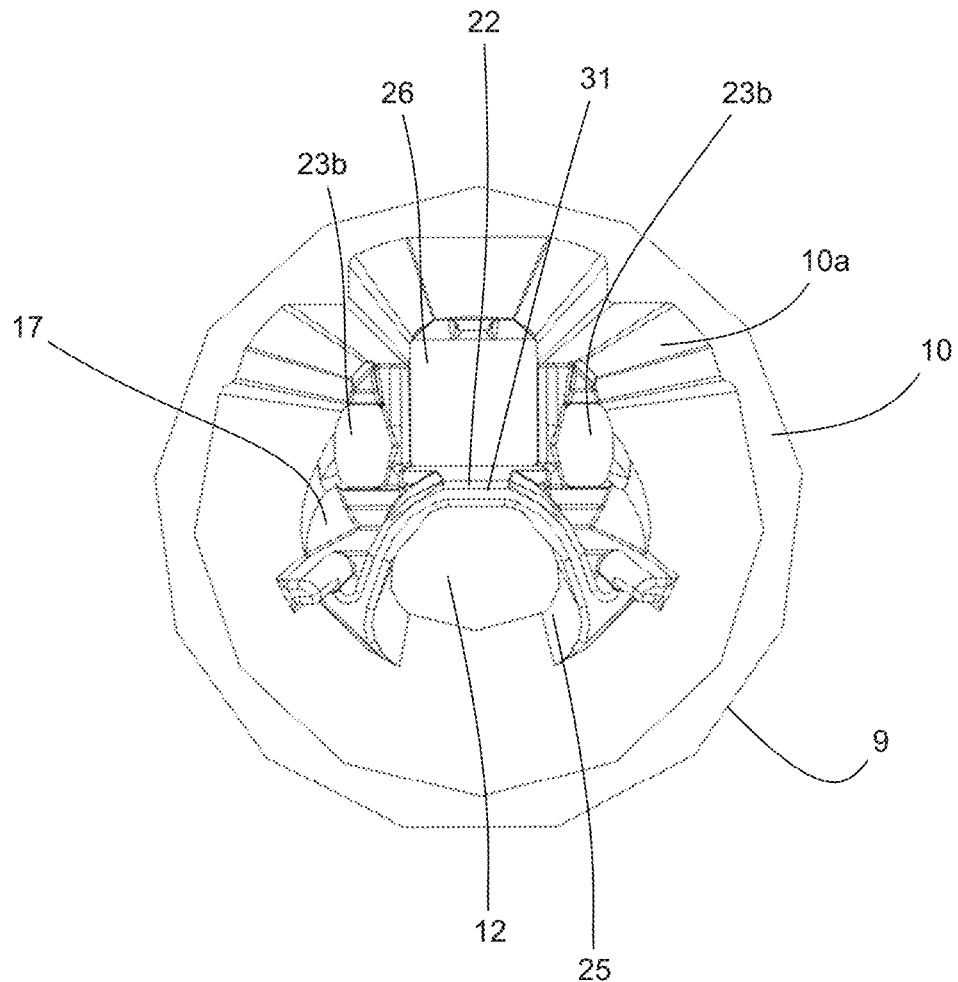
FIG. 8 shows a rear view of the exterior housing of tip part of FIG. 1 without any components inserted.

Referring also to FIGS. 6-8, two light guides 23 are positioned within the camera compartment 17 on each side of the image sensor 18 and lens stack 19. The light guides 23 extend from the closing element 21 to a proximal surface of the distal front wall 11 to be positioned directly proximally of and to abut a light guide window 23b (see FIG. 8) of the distal front wall 11. In an alternative embodiment, the light guide windows may be positioned in the circumferential wall, and the light guides extend thereto. The light guides 23 and light guide windows 23b are positioned with a distance to each other in the transverse direction extending transversely to the proximal-distal direction PD. The distance being more than a largest extent of the image sensor 18 in the transverse direction. The light guides 23 are positioned adjacent and in close proximity to the circumferential wall 10. The light guides 23 are positioned a distance less than a largest extent in the transverse direction of a light guide 23 from the circumferential wall 10. The light guides 23 are preferably formed integrally and in one piece with the closing element 21.

The sealing surface 22 is substantially formed by the circumferential wall 10. Two light sources in the form of LEDs 24 are attached to or abut the closing element 21 and are positioned on a proximal surface 21a of the closing element 21 so as to emit light towards and into the light guides 23. The LEDs 24 are positioned directly proximally of the light guides 23 and on each side of the image sensor 18 and lens stack 19. The light sources 24 are positioned with a distance to each other in the transverse direction, the distance being more than a largest extent of the image sensor 18 in the transverse direction. The light sources 24 are positioned adjacent and in close proximity to the circumferential wall 10 with a distance less than a largest extent in the transverse direction of a light guide 23 from the circumferential wall 10. The light sources 24 are positioned at in the transverse direction opposite sides of the tip part 2.

The exterior housing 9 in FIG. 5 is shown with an optional working channel 25. The exterior housing 9 here comprises a distal part of a working channel 25, the working channel having an opening 12 in the distal front wall 11 of the housing 9. In alternative embodiments, the working channel opening may be in the circumferential wall 10 of the exterior housing 9. The working channel 25 allows fluid to be introduced and/or removed from a body cavity and/or insertion of surgical instruments or the like into the body cavity. The working channel tube 25a (see FIG. 4) may be provided extending from a proximal end 3b of the endoscope 1 to a distal end 3a of the endoscope 1 to guide a tool and/or to provide suction. Alternatively, the working channel may be provided in a second lumen separate of the tip part 2.

The working channel 25 and working channel opening 12 are positioned below a camera window 26, the light guides 23, 23b, the closing element 21, the camera assembly 16, and the PCBs 27. The closing element 21 is shaped to at least partly surround and abut the working channel 25.

The circumferential wall 10 has an inner surface 10a. The sealing surface 22 may be formed by a section of a flexible printed circuit (FPC) 13, the inner surface 10a, and a compartment wall 31 that extends from the distal front wall 11 of the housing 9 toward a proximal end of the camera compartment 17 and further in the distal-proximal direction.

The exterior housing 9 is an outer most wall of the tip 2 and is cup-shaped, the cup-shape being formed by the distal front wall 11 and the circumferential housing wall 10. The distal front wall 11 is the distal most wall of the tip part 2 and defines a distal most part of the tip part 2. The distal front wall 11 is positioned oppositely from the proximal end 14 of the housing 9. The distal front wall 11 coincides with a distal end of the tip part 2. It should be noted that the distal front wall 11 of the tip part 2 need not define a distalmost part of the medical insertion vision device.

The potting compartment 20 is a proximal volume of the interior spacing 15, positioned proximally of the sealing material and the closing element 21. The potting compartment 20 is positioned between the proximal opening 14 of the exterior housing 9 and proximally of the sealing material and closing element 21.

The lens stack 19 may e.g. include three lenses. The lenses are arranged in front of the image sensor 18 so that an optical axis of the lenses align and coincide with an optical axis of the image sensor 18. The lenses are stacked in the proximal-distal direction PD and optically change light to focus light onto the image sensor 21.

The camera window 26 here forms part of the distal front wall 11 and is formed integrally and in one piece with distal front wall 11 and the circumferential wall 10 as is best seen in FIG. 6. As also mentioned earlier, the camera window may in other embodiments form part of the circumferential wall 10. The distal front wall 11 and the circumferential wall 10 form a liquid-tight (except for any potential inlets, outlets, and openings) barrier between an exterior of the tip part 3 or the environment and the interior spacing 15 of the tip part 2. By integrally forming the circumferential wall 10 and distal front wall 11, a sealed tip part 2 is provided.

Referring to FIGS. 6 and 7, a printed circuit board (PCB) 27 is connected and attached to the camera assembly 16. The PCB 27 may comprise an electrical component 29, for example for converting an image signal from the image sensor to an alternative signal. Power to the PCB 27 may be supplied by a power source provided in the handle of the medical insertion vision device. The PCB 27 can then supply power to the LEDs 24.

The FPC 13, which is a part of the PCB 27, extends adjacent to the closing element 21 and abuts the closing element 21 and is pressed against the interior sealing surface 22 by the closing element 21. The FPC 13 is connected to the image sensor 18.

The PCB 27 comprises the LEDs 24 which are positioned to abut and/or are attached to the proximal surface 21*a* of the closing element 21 by a transparent adhesive. As best seen in FIG. 7, the closing element 21 comprises recesses 30 positioned on the proximal surface 21*a* for positioning of the LEDs 24. The recesses 30 and the LEDs 24 are positioned directly proximally of the light guides 23. The recesses 30 are formed integrally and in one piece with the light guides 23 and the closing element 21. A majority of PCB 27 is positioned outside of the camera compartment 17.

Figure 9:
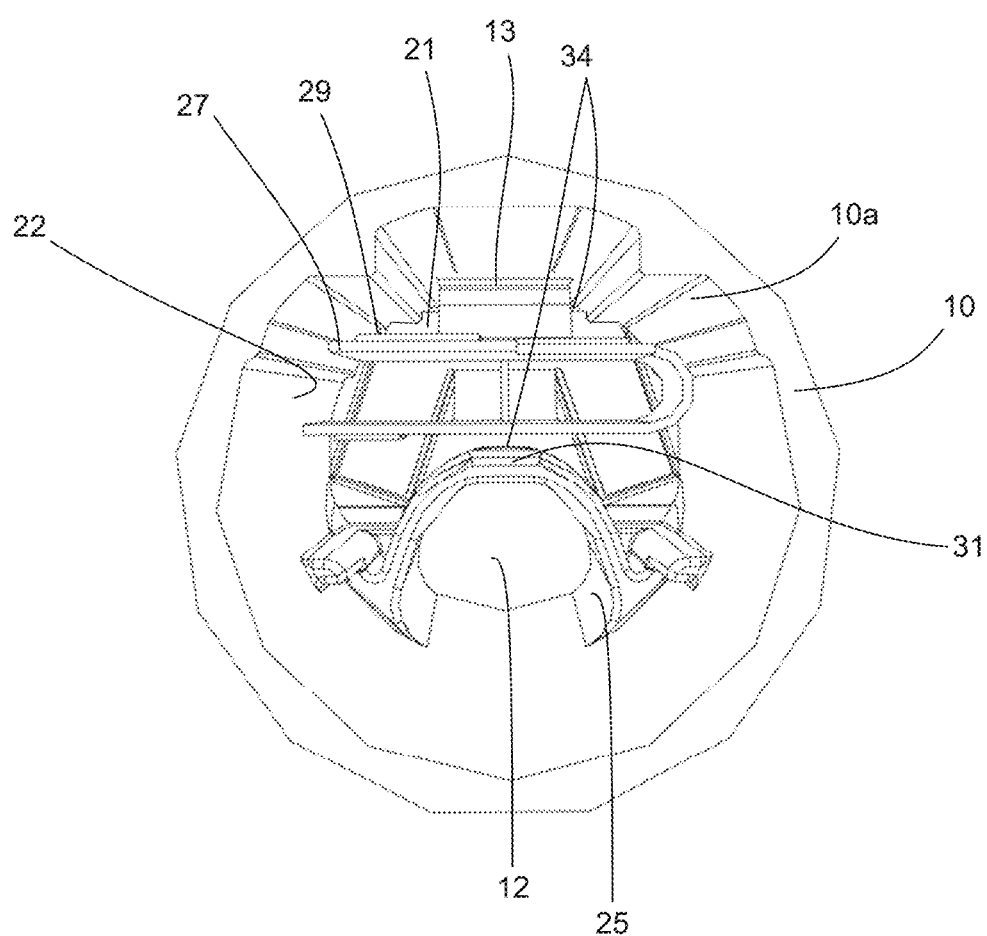
FIG. 9 shows the exterior housing of FIG. 8 with the closing element inserted.

FIG. 8 shows the exterior housing from a proximal viewpoint. FIG. 9 shows the exterior housing from the proximal viewpoint but with the camera assembly and other components inserted in the exterior housing. The sealing surface 22 is substantially formed by the inner surface 10*a* of the circumferential wall 10. The sealing surface 22 in the shown example, is partly formed by a part of the FPC 13. The sealing surface 22 is here optionally also partly formed by a compartment wall 31 that extends from the distal front wall 11 of the housing 9 to a proximal end of the camera compartment 17 and further in the distal-proximal direction. The compartment wall 31 is enclosed by the circumferential wall 10 and is provided in the interior spacing 15. The compartment wall 31 is separate of the circumferential wall 10 and is formed integrally and in one piece with the distal front wall 11. The compartment wall 11 in this embodiment forms a part of an exterior of the working channel 25.

As is best seen in FIG. 9, the closing element 21 substantially covers a cross-sectional area of the camera compartment 17 at the sealing surface 22. The closing element 21 has a cross-sectional shape that is complementary to the shape of the cross-sectional area defined by the sealing surface 22. The closing element 21 is positioned proximally of the image sensor 18 and lens stack 19.

With reference to the figures, a method of manufacture of the tip part 2 according to this disclosure will now be described. First, the exterior housing 9 of the tip part 2 is provided.

Then, the camera assembly 16 is inserted from the open proximal end 14 of the housing 9 into the camera compartment 17, with the lens stack 19 distal of the image sensor 18, preferrably to a final position of camera assembly in the exterior housing in which the camera assembly 16 abuts the camera window 26.

The closing element 21 is inserted, preferably simultaneously, with the camera assembly 16, to be positioned adjacent and proximally of the proximal end 18*a* of the image sensor 18. The closing element 21 acts as a divider between the camera compartment 17 and the potting compartment 20. The proximal surface 21*a* of the inserted closing element 21 extends substantially in the transverse direction. When inserted there is a predetermined sealing gap 34 (best seen in FIG. 9) between the closing element 21 and the sealing surface 22. This sealing gap 34 is preferably as small as possible to prevent sealing material from reaching the camera compartment 17 and interfering with image reception of the camera assembly 16 and light transmission of the LEDs 24, whilst allowing easy insertion of the closing element 21.

Next the camera compartment 17 is sealed forward of the proximal potting compartment 20 of the interior spacing 15 by means of a sealing material. The step of sealing the camera compartment 17 comprises applying the sealing material to cover and thus seal the sealing gap. The sealing material may be applied by cannula. In this example, the sealing material at application is a liquid material and has a higher viscosity than the potting material at application. The sealing material in this example is an acrylated urethane with a viscosity of 1000 cP (1 Pa*s) measured at 25+/−0.2 degrees Celsius with a Brookfield R/S-CPS+ Rheometer (or according to test 6.3 in the standard DS/EN 12092:2001), but may be any sealing material described in the above.

The sealing material is then cured by UV light exposure. Air may surround the components, such as the camera assembly and light guides, in the camera compartment 17.

Followingly, a potting material is potted into the potting compartment 20, the sealing of the camera compartment 17 preventing the potting material from reaching the camera compartment 17. In this example, the potting material at application is a liquid material in the form of an acrylated urethane with a viscosity of 150 cP (0.15 Pa*s) measured at 25+/−0.2 degrees Celsius with a Brookfield R/S-CPS+ Rheometer (or according to test 6.3 in the standard DS/EN 12092:2001), but may be any potting material described in the above. After the potting of the potting material, the potting material does not extend farther distally than to a proximal end 18*a* of the image sensor 18. This potting material is the only potting material present in the tip part 2.

The proximal end 28 of the camera compartment 17 may be positioned a distance CC of ⅔ of the total housing length HL of the housing 9 distally from the proximal open end 14 of the exterior housing 9. The total housing length HL extends in the proximal-distal direction PD.

A working channel tube 25*a* may be inserted into the working channel opening 12 of the tip part 2 before the step of potting the potting material, The step of potting a potting material substantially fills the potting compartment 20 with the potting material.

Figure 10:
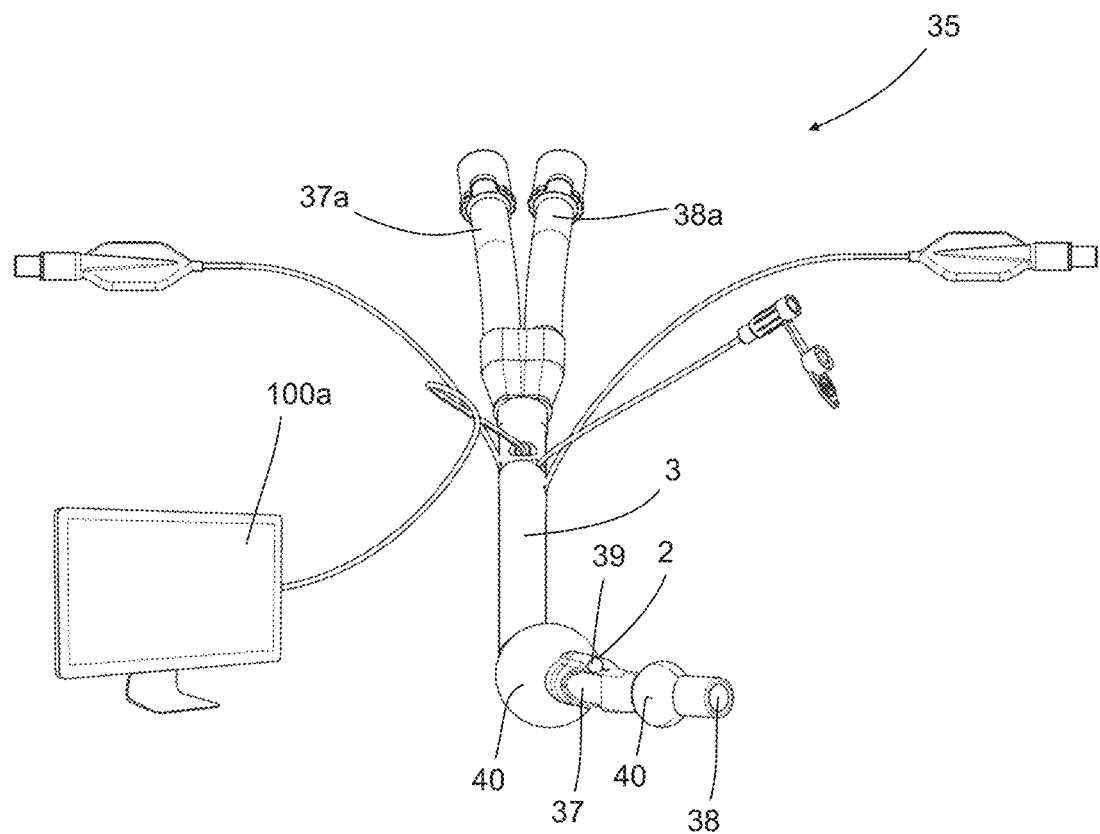
FIG. 10 shows another embodiment of a system comprising an embodiment of a medical insertion vision device in the form of a disposable dual lumen endotracheal tube.

FIG. 10 shows a dual lumen endotracheal tube 35 with a tube 36, first and second lumina 37, 38, and a tip part 2 according to the present invention. The tip part 2 forms a part of a tip of a dedicated camera lumen 39, which is separate of the first and second lumina 37,38 which are working channel lumen (which may also be denoted a catheter lumen). The camera lumen 39 including a distal-most part of the camera lumen 39 is positioned proximally of a distal-most part of the second lumen 38. The camera lumen 39 is positioned externally of the working channel lumina 37,38 and extends along an exterior of the working channel lumina 37, 38. The endotracheal tube 35 further comprises two inflatable cuffs 40 which may be inflated to seal against air leakage and aspiration of gastric contents, blood, secretions, and other fluids, as well as to facilitate retention of the position and ventilation. A cable 8 connects the endotracheal tube to a medical monitor connected to the display 104 allowing images received by the camera assembly of the tip part 2 to be displayed to provide vision of the surroundings of the endotracheal tube and/or allow monitoring of a specific target area within the anatomic body cavity when inserted. In the present embodiment the tip part 2 does not include connections to pull-wires or a working channel, since the housing fits within the camera lumen 39 and the control and power cables are routed through the camera lumen 39 to the proximal end of the endotracheal tube 35. In another variation (see FIG. 11), the endotracheal tube is a single lumen endotracheal tube. For the purposes of this paragraph and the paragraph below, the single and double lumen designations refer to working channel lumens, for example to provide ventilation and access to the esophagus, and the presence of lumens within the wall of the endotracheal tube, such as the camera lumen 39 or a lumen to provide cleaning fluid for a nozzle to clean the camera, do not affect this designation.

Figure 11:
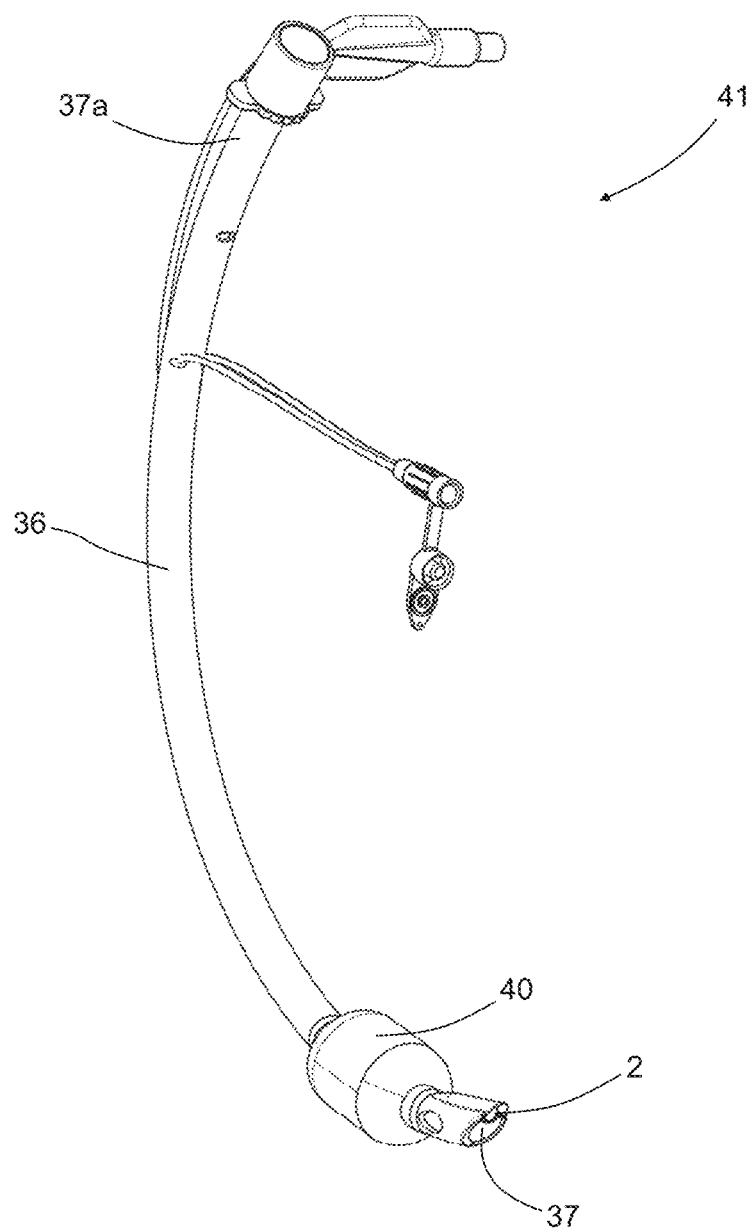
FIG. 11 shows another embodiment of a medical insertion vision device in the form of a disposable single lumen endotracheal endoscope.

FIG. 11 shows yet another possible application of the tip part according to the invention, here in a single lumen endotracheal tube 41 with a single lumen 37, an inflatable cuff 40 according to the invention positioned near a distal end of the tube 36 and lumen 37. Hereby vision of the surrounds of the distal end may be provided during insertion of the endotracheal tube and/or monitoring of a specific target area may be carried out.

Exemplary embodiments of the present disclosure are set out in the following exemplary items:

Item 1. A method of manufacture of a tip part, the tip part being for forming at least part of a tip of a medical insertion vision device, the method comprising: providing an exterior housing of the tip part having an open proximal end for connection to other parts of the medical insertion vision device, such as an insertion tube, the housing further having a distal front wall and a circumferential wall, the circumferential wall extending from the distal front wall to the proximal end of the housing, the distal front wall and the circumferential wall enclosing an interior spacing of the tip part; inserting a camera assembly of the tip part into a distal camera compartment of the interior spacing, the camera assembly comprising an image sensor and a lens stack, the lens stack being positioned distally of the image sensor, whereby the image sensor can provide an image from an object to be investigated; sealing the camera compartment towards a proximal potting compartment of the interior spacing by means of a sealing material; and potting a potting material into the potting compartment, the sealing of the camera compartment preventing the potting material from reaching the camera compartment, the camera compartment containing the lens stack and the image sensor, wherein, after the potting of the potting material, the potting material does not extend farther distally than to a proximal end of the image sensor.

Item 2. A method of manufacture of a tip part according to item 1, wherein a sealing surface is substantially formed by the circumferential wall.

Item 3. A method of manufacture of a tip part according to item 1 or 2, wherein the step of sealing the camera compartment comprises applying the sealing material proximally of the sealing surface.

Item 4. A method of manufacture of a tip part according to any one of the preceding items, further comprising the step of inserting a plate-shaped closing element of the tip part into the camera compartment, the closing element substantially covering a cross-sectional area defined by an interior circumferential sealing surface of the camera compartment, wherein sealing of the camera compartment towards the proximal potting compartment of the interior spacing is by means of the closing element and the sealing material.

Item 5. A method of manufacture of a tip part according to any one of the preceding items, wherein together with the step of inserting the camera assembly, one or more light guides are also inserted into the camera compartment.

Item 6. A method of manufacture of a tip part according any one of the preceding items, wherein parts of the sealed camera compartment not occupied by components of the tip part are air-filled.

Item 7. A tip part for forming at least part of a tip of a medical insertion vision device, the tip part comprising: an exterior housing of the tip part having an open proximal end for connection to other parts of the device, the housing further having a distal front wall and a circumferential wall, the circumferential wall extending from the distal front wall to the proximal end of the housing, the distal front wall and the circumferential wall enclosing an interior spacing of the tip part; and a camera assembly positioned in a distal, air-filled camera compartment of the interior spacing, the camera assembly comprising an image sensor and a lens stack, the lens stack being positioned distally of the image sensor, whereby the image sensor can provide an image from an object to be investigated; wherein the air-filled camera compartment is sealed towards a proximal potting compartment of the interior spacing by means of a sealing material; wherein after a potting material has been potted into the potting compartment, the potting material does not extend farther distally than to a proximal end of the image sensor.

Item 8. A tip part according to item 7, wherein the sealing by the sealing material has prevented the potting material from reaching the camera compartment.

Item 9. A tip part according to any one of items 7 or 8, wherein the potting compartment is defined by a proximal volume of the interior spacing, the proximal volume being positioned proximally of the sealing material, wherein the potting compartment is substantially filled with the potting material.

Item 10. A tip part according to any one of items 7-9, wherein the potting material is in contact with the sealing material.

Item 11. A tip part according to any one of items 7-10, wherein the air-filled camera compartment is sealed towards the proximal potting compartment by means of the sealing material and a plate-shaped closing element covering a cross-sectional area defined by an interior circumferential sealing surface of the camera compartment, and wherein the sealing material is provided proximally of the sealing surface of the camera compartment.

Item 12. A tip part according to any one of items 7-11, wherein one or more light guides are positioned within the camera compartment.

Item 13. A tip part according to item 12, wherein the one or more light guides are formed integrally and in one piece with the closing element.

Item 14. A tip part according to any one of items 11-13, wherein the sealing surface is substantially formed by the circumferential wall.

Item 15. A tip part according to any one of items 11-14, wherein one or more light sources are positioned to abut and/or are attached to the closing element, the one or more light sources potentially being positioned on a proximal surface of the closing element.

Item 16. A tip part according to any one of the items 7-15, wherein the exterior housing comprises at least a part of a working channel, the working channel having an opening in the distal front wall of the housing.

Item 17. A medical insertion vision device comprising a tip part manufactured according to any one of the items 1-6 or comprising a tip part according to any one of the items 7-16.

Item 18. A medical insertion vision device according to item 17, wherein the medical insertion vision device is an endoscope.

Item 19. A medical insertion vision device according to item 17, wherein the medical insertion vision device is a catheter, such as an endotracheal tube, in particular a single lumen or dual lumen endotracheal tube or a feeding probe.

Item 20. A medical insertion vision device according to item 17, wherein the medical insertion vision device is a medical tool comprising a camera.

Item 21. A system comprising: a medical insertion vision device according to any one of items 17-20; and a display for displaying an image provided by the camera assembly of the medical insertion vision device.

LIST OF REFERENCE NUMERALS

1 Endoscope
2 Tip part
3a Distal end
3b Proximal end
4 Insertion tube
4a Outer sheath
5 Handle
6 Control arrangement
7 Bending section
8 Cable
8a Connector
9 Exterior housing
10 Circumferential wall
10a Inner surface
11 Distal front wall
12 Working channel opening
13 Flexible printed circuit (FPC)
14 Open proximal end
15 Interior spacing
16 Camera assembly
17 Camera compartment
17a Sealing material
18 Image sensor
18a Proximal end of image sensor
19 Lens stack
20 Potting compartment
20a Potting material
21 Closing element
21a Proximal surface
22 Sealing surface
23 Light guides
23b Light guide windows
24 Light source
25 Working channel
26 Camera window
27 Printed circuit board (PCB)
28 Open proximal end
29 Electrical component(s)
30 Recess
31 Compartment wall
32 Cable sheath
34 Sealing gap
35 Dual lumen endotracheal tube
36 Tube
37 First lumen
37a Proximal end of first lumen
38 Second lumen
38a Proximal end of Second lumen
39 Camera lumen
40 Inflatable cuff
41 Single lumen endotracheal tube
PD Proximal-distal direction
HL Total exterior housing length
CC Distance

We claim:

1. A method of manufacture of a tip part of a medical insertion vision device, the method comprising:
providing an exterior housing having a proximal end, a distal front wall and a circumferential wall, the circumferential wall extending from the distal front wall to the proximal end of the housing, the distal front wall and the circumferential wall enclosing an interior spacing of the exterior housing, the interior spacing comprising a camera compartment and a potting compartment proximal of the camera compartment;
inserting a camera assembly into the camera compartment, the camera assembly comprising an image sensor and a lens stack positioned distally of the image sensor;
inserting a plate-shaped closing element into the camera compartment proximally of the image sensor, the plate-shaped closing element having a circumferential surface that forms a sealing gap with an interior sealing surface of the camera compartment, the circumferential wall providing at least a portion of the interior sealing surface;
applying a sealing material to seal the camera compartment from the potting compartment; and
potting a potting material proximally of the sealing material, into the potting compartment, the sealing material preventing the potting material from reaching the camera compartment,
wherein, after the potting of the potting material, the potting material does not extend farther distally than to a proximal end of the image sensor.

2. The method of claim 1, wherein the housing comprises a portion of a working channel defined in part by an internal wall separating the portion of the working channel from the camera compartment, the internal wall providing at least a portion of the interior sealing surface.

3. The method of claim 2, wherein applying the sealing material comprises applying the sealing material proximally of the sealing surface.

4. The method of claim 2, wherein the tip part comprises a flexible circuit board connected to the image sensor and extending proximally from the image sensor between the plate-shaped closing element and the circumferential wall.

5. The method of claim 4, wherein one or more light guides extend distally from the plate-shaped closing element and are inserted into the camera compartment with the plate-shaped closing element.

6. The method of claim 1, wherein a free-space of the sealed camera compartment is air-filled.

7. The method of claim 1, wherein, when applied, the sealing material has a viscosity higher than the potting material.

8. The method of claim 7, wherein the potting material comprises the sealing material.

9. A tip part for a medical insertion vision device, the tip part comprising:
an exterior housing having a distal front wall, a proximal end, and a circumferential wall connected to and extending proximally from the distal front wall to the proximal end, the distal front wall and the circumferential wall enclosing an interior spacing of the exterior housing, the interior spacing comprising a camera compartment at a distal end of the exterior housing and a potting compartment proximal of the camera compartment;
a camera assembly positioned in the camera compartment, the camera assembly comprising an image sensor and a lens stack positioned distally of the image sensor, the image sensor having a proximal end;

a plate-shaped closing element in the camera compartment proximally of the image sensor, the plate-shaped closing element having a circumferential surface that forms a sealing gap with an interior sealing surface of the camera compartment, the circumferential wall providing at least a portion of the interior sealing surface;

a sealing material that seals the camera compartment from the potting compartment; and a potting material in the potting compartment proximally of the sealing material, the sealing material preventing the potting material from extending father distally than the proximal end of the image sensor.

10. The tip part of claim 9, wherein a portion of the potting material contacts the sealing material and the sealing material prevents the portion of the potting material from extending into the camera compartment.

11. The tip part of claim 10, wherein a free-space of the potting compartment is filled at least 70% with the potting material.

12. The tip part of claim 9, wherein the sealing material has a higher viscosity than the potting material.

13. The tip part of claim 9, wherein the tip part comprises one or more light guides extending distally from the plate-shaped closing element.

14. The tip part of claim 13, wherein the one or more light guides are formed integrally and in one piece with the plate-shaped closing element.

15. The tip part of claim 14, further comprising one or more light sources aligned with corresponding of the one or more light guides and positioned proximally of the plate-shaped closing element.

16. A medical insertion vision device comprising the tip part of claim 9.

17. The medical insertion vision device of claim 16, wherein the medical insertion vision device is an endoscope.

18. The medical insertion vision device of claim 16, wherein the medical insertion vision device is a catheter, a single lumen endotracheal tube, a dual lumen endotracheal tube or a feeding probe.

19. A medical insertion vision device according to claim 16, wherein the medical insertion vision device is a medical tool.

20. A visualization system comprising:

the medical insertion vision device of claim 16; and a monitor device operable to present images on a display screen, the images provided by the camera assembly of the medical insertion vision device.

21. The visualization system of claim 20, wherein the monitor device comprises a display screen.

22. The tip part of claim 9, wherein the tip part comprises a flexible circuit board connected to the image sensor and extending proximally from the image sensor between the plate-shaped closing element and the circumferential wall, the flexible circuit board providing at least a portion of the interior sealing surface.

23. The tip part of claim 22, wherein the housing comprises a portion of a working channel defined in part by an internal wall separating the portion of the working channel from the camera compartment, the internal wall providing at least another portion of the interior sealing surface.

* * * * *